United States Patent [19]
Maris et al.

[11] Patent Number: 5,844,684
[45] Date of Patent: Dec. 1, 1998

[54] OPTICAL METHOD FOR DETERMINING THE MECHANICAL PROPERTIES OF A MATERIAL

[75] Inventors: Humphrey J. Maris, Barrington, R.I.; Robert J. Stoner, Duxbury, Mass.

[73] Assignee: Brown University Research Foundation, Providence, R.I.

[21] Appl. No.: 808,632

[22] Filed: Feb. 28, 1997

Related U.S. Application Data

[60] Provisional application Nos. 60/017,481 Apr. 26, 1996 and 60/017391 May 8, 1996.

[51] Int. Cl.[6] .......................... G01N 21/00; G01N 21/55
[52] U.S. Cl. ............................................ 356/432; 356/445
[58] Field of Search ............................... 356/432 I, 445

[56] References Cited

U.S. PATENT DOCUMENTS

| | | | |
|---|---|---|---|
| 3,950,987 | 4/1976 | Slezinger et al. | 73/141 A |
| 4,484,820 | 11/1984 | Rosencwaig | 374/6 |
| 4,522,510 | 6/1985 | Rosencwaig et al. | 374/7 |
| 4,579,463 | 4/1986 | Rosencwaig et al. | 374/57 |
| 4,632,561 | 12/1986 | Rosencwaig et al. | 356/432 |
| 4,636,088 | 1/1987 | Rosencwaig et al. | 374/5 |
| 4,679,946 | 7/1987 | Rosencwaig et al. | 374/5 |
| 4,710,030 | 12/1987 | Tauc et al. | 356/432 T |
| 4,750,822 | 6/1988 | Rosencwaig et al. | 356/445 |
| 4,795,260 | 1/1989 | Schuur et al. | 356/400 |
| 4,854,710 | 8/1989 | Opsal et al. | 356/432 |
| 4,952,063 | 8/1990 | Opsal et al. | 356/432 |
| 4,999,014 | 3/1991 | Gold et al. | 356/382 |
| 5,042,951 | 8/1991 | Gold et al. | 356/369 |
| 5,042,952 | 8/1991 | Opsal et al. | 356/432 |
| 5,074,669 | 12/1991 | Opsal | 356/445 |
| 5,083,869 | 1/1992 | Nakata et al. | 356/432 |
| 5,379,109 | 1/1995 | Gaskill et al. | 356/445 |
| 5,546,811 | 8/1996 | Rogers et al. | 73/800 |
| 5,574,562 | 11/1996 | Fishman et al. | 356/432 |
| 5,585,921 | 12/1996 | Pepper et al. | 356/357 |

OTHER PUBLICATIONS

W. Lee Smith et al. "Ion implant monitoring with thermal wave technology". Appl. Phys.Lett.. vol. 47 No. 6, Sep. 15, 1985. pp. 584–586.

J. Opsal et al. "Thermal and plasma wave depth profiling in silicon". Appl. Phys. Lett. vol. 47 No. 5, Sep. 1, 1985. pp. 498–500.

A. Rosencwaig et al. "Thin–film thickness measurments with thermal waves". Appl. Phys. Lett., vol. 43 No. 2, Jul. 15, 1983. pp. 166–168.

A Rosencwaig et al. "Detection of thermal waves through optical reflectance". Appl. Phys. Lett., vol. 46 No. 11, Jun. 1, 1985. pp. 1013–1015.

A. Elci et al. "Physics of Ultrafast Phenomena in Solid State Plasmas". Solid–State Electronics, vol. 21, 1978, pp. 151–158.

(List continued on next page.)

*Primary Examiner*—Vincent P. McGraw
*Attorney, Agent, or Firm*—Perman & Green, LLP

[57] ABSTRACT

Disclosed is a method for characterizing a sample, comprising the steps of: (a) acquiring data from the sample using at least one probe beam wavelength to measure, for times less than a few nanoseconds, a change in the reflectivity of the sample induced by a pump beam; (b) analyzing the data to determine at least one material property by comparing a background signal component of the data with data obtained for a similar delay time range from one or more samples prepared under conditions known to give rise to certain physical and chemical material properties; and (c) analyzing a component of the measured time dependent reflectivity caused by ultrasonic waves generated by the pump beam using the at least one determined material property. The first step of analyzing may include a step of interpolating between reference samples to obtain an intermediate set of material properties. The material properties may include sound velocity, density, and optical constants. In one embodiment, only a correlation is made with the background signal, and at least one of the structural phase, grain orientation, and stoichiometry is determined.

55 Claims, 13 Drawing Sheets

OTHER PUBLICATIONS

D.H. Auston et al. "Picosecond Spectroscopy of Semiconductors". Solid–State Electronics, vol. 21, 1978, pp. 147–150.

D. H. Auston et al. "Picosecond Ellipsometry of Transient Electron–Hole Plasmas in Geranium". Physical Review Letters, vol. 32 No. 20. May 20, 1974 pp. 1120–1123.

R.J. Stoner et al. "Kapitza conductance and heat flow between solids at temperatures from 50 to 300K". Physical Review B, vol. 48, No. 22, Dec. 1, 1993 pp. 16 373–16 387.

R.J. Stoner et al. "Measurments of the Kapitza Conductance between Diamond and Several Metals". Physical Review Letters, vol. 68 No. 10, Mar. 9, 1992 pp. 1563–1566.

S. Sumie et al. "A New Method of Photothermal Displacement Measurement by Laser Interferometric Probe". Jpn. J. Appl. Phys. vol. 31 Pt. 1, No. 11, 1992 pp. 3575–3583.

S. Sumie et al. J.Appl. Phys. 76(10), Nov. 15, 1994 pp. 5681–5689.

F.E. Doany et al. "Carrier lifetime versus ion–implantation dose in silicon on sapphire". Appl. Phys. Lett. 50(8), Feb. 23, 1987 pp. 460–462.

D.A. Young et al. "Heat Flow in Glasses on a Picosecond Timescale". Dept. of Engineering, Brown University, Providence, RI. 1986. pp. 49–51.

H.T. Grahn et al., "Time–resolved study of vibrations of a Ge:H/aSi:H multilayers", Phys. Review B, vol. 38, No. 9, Sep. 15, 1988.

H.T. Grahn et al., "Sound velocity and index of refraction of AlAs measured by picosecond ultrasonics", Appl. Phys. Lett. 53, Nov. 21, 1988.

H.T. Grahn et al., "Elastic properties of silicon oxynitride films determined by picosecond acoustics", App. Phys. Lett. 53, Dec. 5, 1988.

H.T. Grahn et al., "Picosecond Ulstrasonics", IEEE, vol. 25, #12, Dec. 1989.

H.N. Lin, et al., "Nondestructive Testing of Microstructures by Picosecond Ultrasonics" Journal of Non–Destructive Evaluation, vol. 9 No. 4, 1990.

H.N. Lin et al., "Phonon Attenuation and Velocity Measurements in Transparent Materials by Picosecond Acoustic Interferometry", Journal of Applied Physics, vol. 69, Apr. 1, 1990.

T.C. Zhu et al., Attenuation of longitudinal–acoustic phonons in amorphous $SiO_2$ at frequencies up to 440 GHz, Physical Review B, vol. 44, #9, Sep. 1, 1991.

H.N. Lin et al., Ultrasonic Experiments At Ultra–High Frequency with Picosecond Time–Resolution, IEEE Ultrasonics Symp. 90.

H.N. Lin et al., "Detection of Titatium Silicide Formation and Phase Transportation by Picosecond Ultrasonics," MRS.

G. Tas et al., "Detection Of thin Interfacial Layers By Picosecond Ultrasonics", Mat. Res. Soc. Symp. Proc. vol. 259, 1992.

G. Tas et al., "Noninvasive picosecond ultrasonic detection of ultrathin interfacial layers: $CF_x$ at the Al/Si interface", Appl. Phys. Lett. 61, Oct. 12, 1992.

H. N. Lin et al., "study of vibrational modes of gold nanostructures by picosecond ultrasonics", J. Appl. Phys. 73, Jan. 1, 1993.

H.J. Maris et al., Picosecond Optics Studies of Vibrational and Mechanical Properties of Nanostructures, AMD–vol. 140, Acousto–Optics and Acoustic Microscopy, ASME 1992.

C.J. Morath et al., "Picosecond optical studies of amorphous diamond and diamondlike carbon: Thermal conductivity and longitudinal sound velocity", J. Appl. Phys. 76, Sep. 1, 1994.

H.N. Lin et al., "Nondestructive detection of titanium disilicide phase transformation by picosecond ultrasonics", IBM T. J. Watson Research Center (no date given).

H.T. Grahn et al., "Picosecond Photoinduced Electronic and Acoustic Effects In a Si:H Based Multilayer Structures", Journal of Non–Crystalline Solids 97&98, 1987.

G. Tas et al., "Picosecond Ultrasonic Investigation of Thin Interfacial Layers Between Films and a Substrate", IBM T. J. Watson Research Center no date given.

H.J. Maris et al., "Studies of High–Frequency Acoustic Phonons Using Picosecond Optical Techniques", Dept. of Physics, Brown University no date given.

C. Thomsen et al., "Processing Acoustics As A Non–Destructive Tool For the Characterization Of Very Thin Films", Thin Solid Films 154 (1987).

P.A. Elzinga et al., "Pump/probe method for fast analysis of visible spectral signatures utlizing asynchronous optical sampling", Applied Optics, vol. 26, No. 19, Oct. 1, 1987.

R. J. Kneisler et al., "Asynchronous optical sampling: a new combustion diagnostic for potential use in turbulent, high–pressure flames", 1989 Optics Letters, vol. 14, No. 5.

C. Thomsen et al., "Surface generation and detection of phonons by a picosecond light pulses", Physical Review B, vol. 34, No. 6, Sep. 16, 1986.

G.J. Flechtner et al., "Measurements of atomic sodium in flames by asynchronous optical sampling: theory and experiment", Applied Optics, vol. 31, No. 15, May 20, 1992.

O.B. Wright, et al."Characterization Of Transparent And Opaque Thin Films Using Laser Picosecond Ultrasonics", Nondestr. Test Eval. vol. 7, pp. 149–163.

O.B. Wright, "Thickness and sound velocity measurement in thin transparent films with laser picosecond acoustics", Journal of Applied Physics, vol. 71, #4, Feb. 15, 1992.

O.B. Wright, et al., "High Resolution Laser Picosecond Acoustics In Thin Films", Symp. on Physical Acodstics, Belgium, 1990.

O.B. Wright et al., "Laser Picosecond Acoustics in Various Types of Thin Film", Japanese Journal of Applied Physics, vol. 31 (1992).

C.A. Paddock et al., "Transient thermoflectance from thin metal films", J. Appl. Phys. 60, Jul. 1, 1986.

D.M. Pennington et al., "Direct Measurement of the Thermal Expansion of a Surface Using Transient Gratings", Optical Society no date given.

K. A. Svinarich et al., "Picosecond Acoustic Pulse Reflection From a Metal–Metal Interface", Dept. of Physicsm Wayne State university no date given.

G.L. Eesley et al., "Generation and detecting of picosecond acoustic pulses in thin metal films", Appl. Phys. Lett. 50, Mar. 23, 1987.

B.M. Clemens et al., "Relationship between Interfacial Strain and the Elastic Response of Multilayer Metal Films", Physical Review Letter, vol. 61, No. 20, Nov. 14, 1988.

OPTICAL METHOD FOR DETERMINING THE MECHANICAL PROPERTIES OF A MATERIAL

STATEMENT OF GOVERNMENT RIGHTS

This invention was made with government support under grant/contract number DEFG02-86ER45267 awarded by the Department of Energy and grant/contract number DMR-9121747 awarded by the National Science Foundation. The government has certain rights in the invention.

This application claims the benefit of U.S. Provisional application(s) Ser. No(s). 60/017,481 Apr. 26, 1996, 60/017,391 May 8, 1996.

CLAIM OF PRIORITY FROM COPENDING PROVISIONAL PATENT APPLICATIONS

Priority is herewith claimed under 35 U.S.C. §119 (e) from copending Provisional Patent Application 60/017,481, filed Apr. 26, 1996, entitled "Optical Method for Determining the Mechanical Properties of a Material", by Humphrey J. Maris and Robert J. Stoner. Priority is herewith also claimed under 35 U.S.C. §119 (e) from copending Provisional Patent Application 60/017,391, filed May 8, 1996, entitled "Optical Method for Determining the Mechanical Properties of a Material", by Humphrey J. Maris and Robert J. Stoner. The disclosures of both of these Provisional Patent Applications are incorporated by reference herein in their entireties.

FIELD OF THE INVENTION

This invention relates generally to a method and apparatus for characterizing a sample using electromagnetic radiation.

BACKGROUND OF THE INVENTION

Presently, the nondestructive evaluation of thin films and interfaces is of interest to manufacturers of electrical, optical and mechanical devices which employ thin films. In one nondestructive technique a radio frequency pulse is applied to a piezoelectric transducer mounted on a substrate between the transducer and the film to be studied. A stress pulse propagates through the substrate toward the film. At the boundary between the substrate and the film, part of the pulse is reflected back to the transducer. The remainder enters the film and is partially reflected at the opposite side to return through the substrate to the transducer. The pulses are converted into electrical signals, amplified electronically, and displayed on an oscilloscope. The time delay between the two pulses indicates the film thickness, if the sound velocity in the film is known, or indicates the sound velocity, if the film thickness is known. Relative amplitudes of the pulses provide information on the attenuation in the film or the quality of the bond between the film and the substrate.

The minimum thickness of films which can be measured and the sensitivity to film interface conditions using conventional ultrasonics is limited by the pulse length. The duration of the stress pulse is normally at least 0.1 $\mu$sec corresponding to a spatial length of at least $3 \times 10^{-2}$ cm for an acoustic velocity of $3 \times 10^5$ cm/sec. Unless the film is thicker than the length of the acoustic pulse, the pulses returning to the transducer will overlap in time. Even if pulses as short in duration as 0.001 $\mu$sec are used, the film thickness must be at least a few microns.

Another technique, acoustic microscopy, projects sound through a rod having a spherical lens at its tip. The tip is immersed in a liquid covering the film. Sound propagates through the liquid, reflects off the surface of the sample, and returns through the rod to the transducer. The amplitude of the signal returning to the transducer is measured while the sample is moved horizontally. The amplitudes are converted to a computer-generated photograph of the sample surface. Sample features below the surface are observed by raising the sample to bring the focal point beneath the surface. The lateral and vertical resolution of the acoustic microscope are approximately equal.

Resolution is greatest for the acoustic microscope when a very short wavelength is passed through the coupling liquid. This requires a liquid with a low sound velocity, such as liquid helium. An acoustic microscope using liquid helium can resolve surface features as small as 500 Angstroms, but only when the sample is cooled to 0.1 K.

Several additional techniques, not involving generation and detection of stress pulses, are available for measuring film thickness. Ellipsometers direct elliptically polarized light at a film sample and analyze the polarization state of the reflected light to determine film thickness with an accuracy of 3–10 Angstroms. The elliptically polarized light is resolved into two components having separate polarization orientations and a relative phase shift. Changes in polarization state, beam amplitudes, and phase of the two polarization components are observed after reflection.

The ellipsometer technique employs films which are reasonably transparent. Typically, at least 10% of the polarized radiation must pass through the film. The thickness of metal sample films thus cannot exceed a few hundred Angstroms.

Another technique uses a small stylus to mechanically measure film thickness. The stylus is moved across the surface of a substrate and, upon reaching the edge of a sample film, measures the difference in height between the substrate and the film. Accuracies of 10–100 Angstroms can be obtained. This method cannot be used if the film lacks a sharp, distinct edge, or is too soft in consistency to accurately support the stylus.

Another non-destructive method, based on Rutherford Scattering, measures the energy of backscattered helium ions. The lateral resolution of this method is poor.

Yet another technique uses resistance measurements to determine film thickness. For a material of known resistivity, the film thickness is determined by measuring the electrical resistance of the film. For films less than 1000 Angstroms, however, this method is of limited accuracy because the resistivity may be non-uniformly dependent on the film thickness.

In yet another technique, the change in the direction of a reflected light beam off a surface is studied when a stress pulse arrives at the surface. In a particular application, stress pulses are generated by a piezoelectric transducer on one side of a film to be studied. A laser beam focused onto the other side detects the stress pulses after they traverse the sample. This method is useful for film thicknesses greater than 10 microns.

A film may also be examined by striking a surface of the film with an intense optical pump beam to disrupt the film's surface. Rather than observe propagation of stress pulses, however, this method observes destructive excitation of the surface. The disruption, such as thermal melting, is observed by illuminating the site of impingement of the pump beam with an optical probe beam and measuring changes in intensity of the probe beam. The probe beam's intensity is altered by such destructive, disruptive effects as boiling of the film's surface, ejection of molten material, and subsequent cooling of the surface. See Downer, M. C.; Fork, R. L.; and Shank, C. V., "Imaging with Femtosecond Optical Pulses", Ultrafast Phenomena IV, Ed. D. H. Auston and K. B. Eisenthal (Spinger-Verlag, N.Y. 1984), pp. 106–110.

Other systems measure thickness, composition or concentration of material by measuring absorption of suitably-chosen wavelengths of radiation. This method is generally applicable only if the film is on a transparent substrate.

In a nondestructive ultrasonic technique described in U.S. Pat. No. 4,710,030 (Tauc et al.), a very high frequency sound pulse is generated and detected by means of an ultrafast laser pulse. The sound pulse is used to probe an interface. The ultrasonic frequencies used in this technique typically are less than 1 THz, and the corresponding sonic wavelengths in typical materials are greater than several hundred Angstroms. It is equivalent to refer to the high frequency ultrasonic pulses generated in this technique as coherent longitudinal acoustic phonons.

In more detail, Tauc et al. teach the use of pump and probe beams having durations of 0.01 to 100 psec. These beams may impinge at the same location on a sample's surface, or the point of impingement of the probe beam may be shifted relative to the point of impingement of the pump beam. In one embodiment the film being measured can be translated in relation to the pump and probe beams. The probe beam may be transmitted or reflected by the sample. In a method taught by Tauc et al. the pump pulse has at least one wavelength for non-destructively generating a stress pulse in the sample. The probe pulse is guided to the sample to intercept the stress pulse, and the method further detects a change in optical constants induced by the stress pulse by measuring an intensity of the probe beam after it intercepts the stress pulse.

In one embodiment a distance between a mirror and a corner cube is varied to vary the delay between the impingement of the pump beam and the probe beam on the sample. In a further embodiment an opto-acoustically inactive film is studied by using an overlying film comprised of an opto-acoustically active medium, such as arsenic telluride. In another embodiment the quality of the bonding between a film and the substrate can be determined from a measurement of the reflection coefficient of the stress pulse at the boundary, and comparing the measured value to a theoretical value.

The methods and apparatus of Tauc et al. are not limited to simple films, but can be extended to obtaining information about layer thicknesses and interfaces in superlattices, multilayer thin-film structures, and other inhomogeneous films. Tauc et al. also provide for scanning the pump and probe beams over an area of the sample, as small as 1 micron by 1 micron, and plotting the change in intensity of the reflected or transmitted probe beam.

While well-suited for use in many measurement applications, it is an object of this invention to extend and enhance the teachings of Tauc et al.

More particularly, for situations in which the material properties (i.e. sound velocity, density, optical constants etc.) are known with adequate precision (for example, because the deposition source is known to be pure, and the deposition process is known to give highly repeatable grain structure and structural phase), fitting may be performed using predetermined values for many of the material properties (such as density, sound velocity, optical constants) in order to determine a sample characteristic of interest (such as thickness, or adhesion strength). This is often a preferred approach for samples containing pure metal films since it is computationally efficient, and therefore allows measurements to be made quickly.

However, this approach can lead to inaccurate results for samples containing films whose material properties (for example, sound velocity, density and optical constants) may be affected by deposition conditions such as temperature, gas mixture, and substrate species. In such cases it may not be possible to unambiguously determine the contributions to the time dependence of the detected probe signal due to the sample thickness and sound velocity.

OBJECTS OF THE INVENTION

It is a first object of this invention to provide an improved method for the non-destructive evaluation of materials that overcomes the foregoing and other problems.

It is a further object of this invention to provide a two step method to analyze data obtained with pump and probe optical beams, wherein a background signal is employed to determine mechanical properties of a material, and wherein a component of a measured time dependent change in an optical property generated by the pump beam, such as the reflectivity ($\Delta R(t)$), is analyzed using the determined material properties.

SUMMARY OF THE INVENTION

Disclosed herein is a method for characterizing a sample, comprising the steps of: (a) acquiring data from the sample using at least one probe beam wavelength to measure, for times less than a few nanoseconds, a transient change in an optical response, such as the reflectivity, of the sample induced by a pump beam; (b) analyzing the data to determine at least one material property by comparing a background signal component of the data with data obtained for a similar delay time range from one or more samples prepared under conditions known to give rise to certain physical and chemical material properties; and (c) analyzing a component of the transient response of the probe beam that is caused by ultrasonic waves generated by the pump beam, using the at least one determined material property. The first step of analyzing may include a step of interpolating between reference samples to obtain an intermediate set of material properties.

The step of acquiring is accomplished with a non-destructive system and method for measuring at least one transient response of the sample to a pump pulse of optical radiation, the measured transient response or responses can include at least one of a measurement of a modulated change $\Delta R$ in an intensity of a reflected portion of a probe pulse, a change $\Delta T$ in an intensity of a transmitted portion of the probe pulse, a change $\Delta P$ in a polarization of the reflected probe pulse, a change $\Delta \phi$ in an optical phase of the reflected probe pulse, and a change in an angle of reflection $\Delta \beta$ of the probe pulse, each of which may be considered as a change in a characteristic of a reflected or transmitted portion of the probe pulse. The measured transient response or responses are then associated with at least one characteristic of interest of the sample.

In one embodiment an association is made with a characteristic such as at least one of the structural phase, grain orientation, and stoichiometry.

This invention also teaches a method for characterizing a sample, comprising the steps of: (a) acquiring data from the sample using at least one probe beam wavelength to measure, for times less than a few nanoseconds, a transient change in the optical response of the sample induced by a pump beam; (b) analyzing the data to determine at least a sample preparation technique by comparing a background signal component of the data with data obtained for a similar delay time range from one or more samples prepared by similar sample preparation techniques; and (c) analyzing a component of the measured time dependent reflectivity caused by ultrasonic waves generated by the pump beam using data corresponding to the determined sample preparation technique.

Further in accordance with this invention a method is taught for characterizing a sample, comprising the steps of: (a) acquiring data from the sample using at least one probe beam wavelength to measure, for a range of delay times, a change in at least one transient optical response of the sample induced by a pump beam; (b) assuming a value for a thickness of the film; (c) comparing a background signal, resulting from a non-acoustical component of the acquired data, to data that corresponds to a film of the same general type having the assumed thickness, to determine a most probable composition for the film; and (d) associating determined physical properties of the film as a result of the execution of step (c) with the sample film. The method further comprises the steps of (e) deducing an improved value for the thickness from an analysis of the acoustical component of the acquired data; and (f) repeating steps c–e until convergence between film thickness and material properties is achieved.

This invention also encompasses a method of characterizing a sample that includes the steps of: (a) acquiring data from the sample using at least one probe beam wavelength to measure, for a range of delay times, a change in at least one transient optical response of the sample induced by a pump beam; (b) assuming a composition of the film; (c) deducing a value for a thickness of the film from an analysis of an acoustical part of the data, the step of deducing including a step of considering the film's material properties based on a film having the assumed composition; and (d) comparing a background signal corresponding to a film of the same general type, having the deduced thickness, to determine an improved composition for the film. The method further includes the steps of (e) associating material properties of the film from step (d) with the sample film; and (f) repeating steps c–e until convergence between the sample film's composition and thickness is achieved.

BRIEF DESCRIPTION OF THE DRAWINGS

The above set forth and other features of the invention are made more apparent in the ensuing Detailed Description of the Invention when read in conjunction with the attached Drawings, wherein.

DETAILED DESCRIPTION OF THE INVENTION

The teaching of this invention, as described in detail below, can be used in conjunction with the teaching of Tauc et al. to augment the characterization of samples, although the use of this or a similar non-destructive, optically-based system should not be construed as a limitation upon the practice of this invention.

In accordance with the teaching of this invention, a light pulse is directed onto a sample, and is partially absorbed by electronic carriers in the sample, which subsequently transfer their energy to the materials comprising the sample. This gives rise to a small, localized increase in the temperature of the sample. Associated with the increase in the temperature of the sample is a small, localized transient change in the sample's optical response. That is, there is manifested at least one transient and measurable response of the sample to the pump pulse of optical radiation. A measured transient response or responses can include at least one of a measurement of a modulated change $\Delta R$ in an intensity of a reflected portion of a probe pulse, a change $\Delta T$ in an intensity of a transmitted portion of the probe pulse, a change $\Delta P$ in a polarization of the reflected probe pulse, a change $\Delta \phi$ in an optical phase of the reflected probe pulse, and a change in an angle of reflection $\Delta \beta$ of the probe pulse, each of which may be considered as a change in a characteristic of a reflected or transmitted portion of the probe pulse. The transient response of the sample to the pump pulse decays at a rate which depends mainly on the rates at which the excited electronic carriers transfer their energy to the remainder of the sample, and also on the thermal diffusivities and thicknesses of the materials comprising the sample.

As disclosed previously by Tauc et al., a second effect of the light pulse may be to generate ultrasonic waves in the sample. These ultrasonic waves also give rise to changes in the optical reflectivity of the sample which vary more rapidly in time than the reflectivity changes associated with the sample's return to thermal equilibrium. In a typical sample the reflectivity changes associated with the ultrasonic waves and with the change in temperature occur concomitantly.

Figure 2:
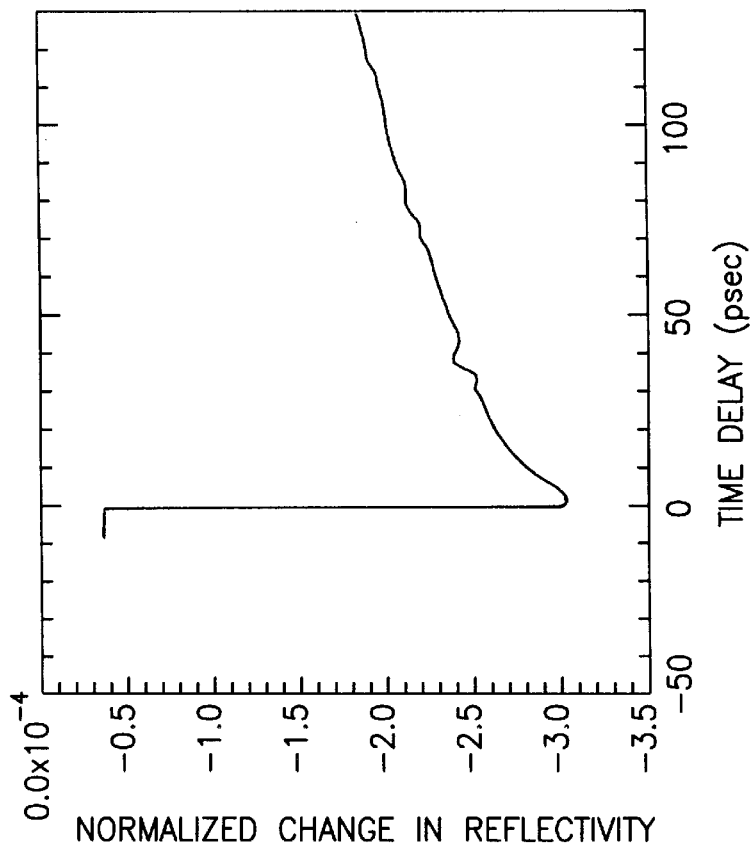
FIG. 2 is a graph illustrating representative data showing acoustic echoes superimposed on a background signal.

Herein, all transient changes in the optical response of the sample, such as the reflectivity, and excluding the ultrasonic contribution, are referred to as the "background" signal. Accordingly, the ultrasonic component of the net reflectivity change may be said to ride on a thermal "background" signal. Typical data are illustrated in FIG. 2. The reflectivity changes associated with the propagating ultrasonic waves may be analyzed in the manner disclosed by Tauc et al. to determine the mechanical properties of a sample.

The reflectivity change is measured by means of a second light pulse, the "probe", which is delayed relative to the heating pulse, the "pump", by a time $\tau$. The value of $\tau$ is typically in the range of 0.01 picosecond to 100 nanoseconds. The sign, magnitude, and rate of decay of the "background" reflectivity change depends on the wavelength, angle of incidence and polarization of the probe light pulse, and on the electronic and thermal properties of the sample material. Thus, the background reflectivity change for samples of the same material may differ substantially due to different preparation conditions. By example, the inventors have observed that different background signals arise for samples composed of the same metal, but having a different structural phase, and also for alloys having differing compositions. These observations are indicative of the differences which exist between the thermal and electronic properties of such materials.

In addition to the intrinsic electronic and thermal properties, the factors referred to above (structural phase, alloy content, impurity concentration, stoichiometry, phase mixture, grain orientation, etc.) may affect the elastic properties of a sample material. For example, the elastic constants and densities of two structural phases of a particular metal may differ significantly, corresponding to readily observed differences in the sound velocity and volume of samples having identical stoichiometry. Similar differences may be seen for samples such as thin films which have been deposited under conditions leading to different grain orientations and shapes.

Consequently, it is desirable that at least one of these parameters be known in advance when making a "best-fit" analysis. This invention provides a method for obtaining greater accuracy, than that obtained by previous techniques, by removing possible ambiguities.

Figure 4:
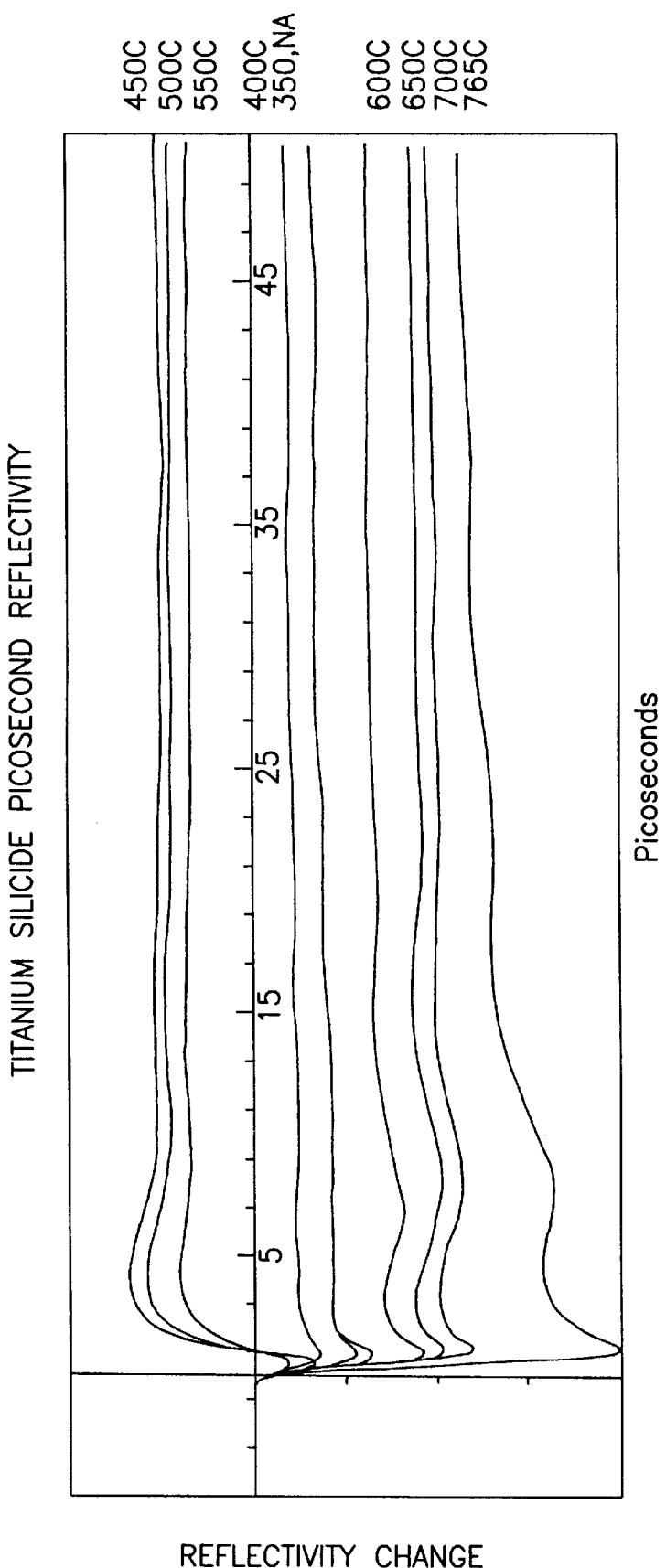
FIG. 4 is a graph illustrating picosecond reflectivity versus time for Ti-Si films annealed at temperatures ranging from 350° C. to 765° C., wherein a result for an unannealed sample, which overlaps the 350° C. curve, is also shown.

In accordance with the teachings of this invention, data are acquired according to methods and apparatus described below by using at least one probe wavelength to measure, for times generally less than a few nanoseconds, a transient change in an optical property, such as the reflectivity, of the sample induced by the pump laser. Referring also to FIG. 4, the data are then analyzed in two steps as follows.

In Step 1, the "background" signal is compared with data obtained for a similar delay time range from samples prepared under conditions known to give rise to certain physical and chemical material properties, such as, by example, structural phase. This may involve interpolation between reference samples to obtain an intermediate set of material properties. Properties including sound velocity, density, optical constants etc. are then associated with the sample of interest.

It should be noted that the background signal can be compared also, or instead, with results obtained from a modeled diffusion process and the associated physical parameters, such as the thermal reflectance.

In Step 2, one or more sample characteristics of interest, such as sound velocity, film thickness, film adhesion, etc., are determined from the measured time dependent change in the optical property, such as reflectivity, caused by the ultrasonic waves generated by the pump beam. These are analyzed in accordance with the material properties determined in Step 1.

As such, the present invention provides a method for obtaining greater accuracy by removing possible ambiguities.

Furthermore, a correlation can be made with a characteristic of the sample preparation technique, rather than a material property per se. For example, the sound velocity appropriate to CVD (Chemical Vapor Deposition) TiN may be different than the sound velocity appropriate to sputtered TiN.

EXAMPLE

Figure 5:
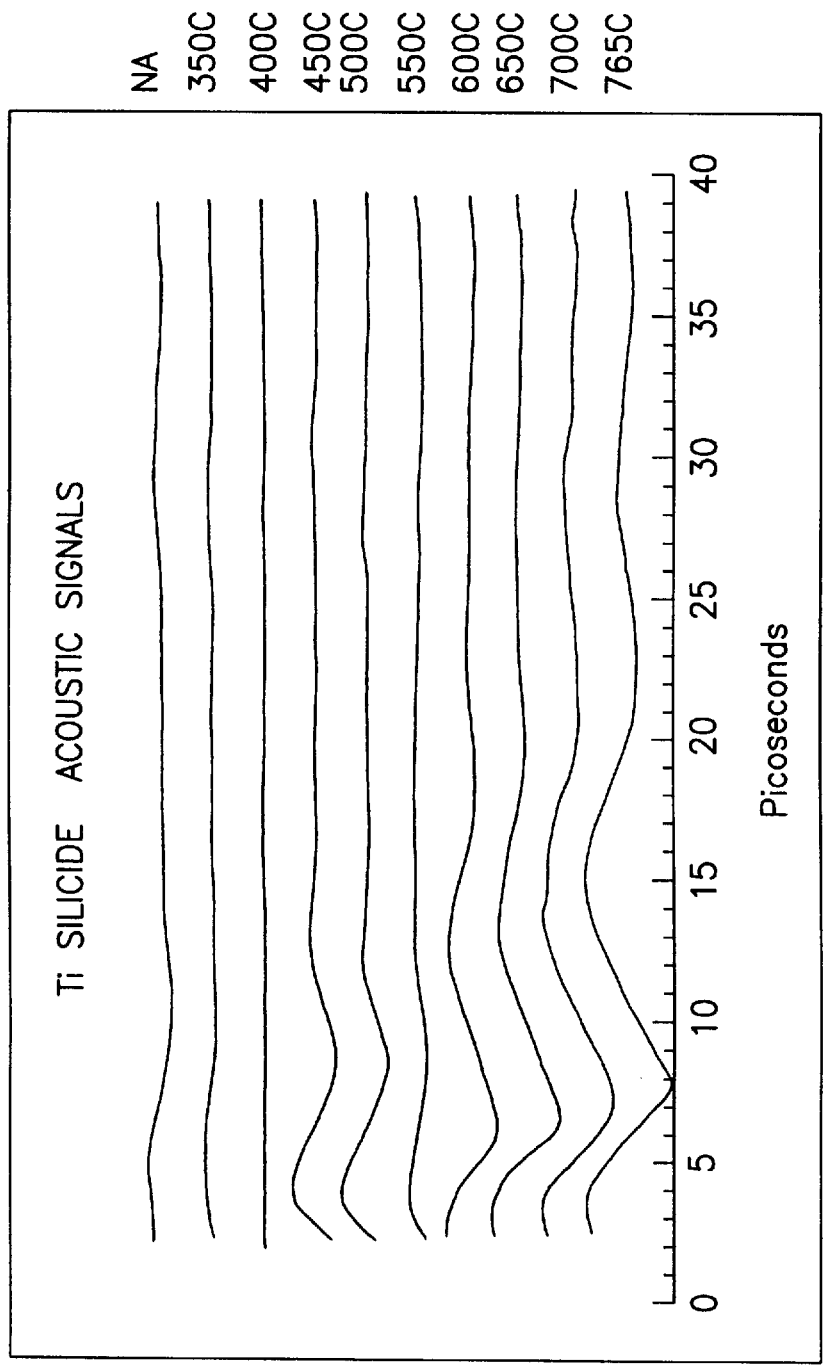
FIG. 5 is a graph showing curves that correspond to the curves shown in FIG. 4, but from which a slowly varying background signal has been removed in order to emphasize the acoustical vibrations of the Ti-Si film, wherein the curves are offset from one another for the sake of clarity.
Figure 6:
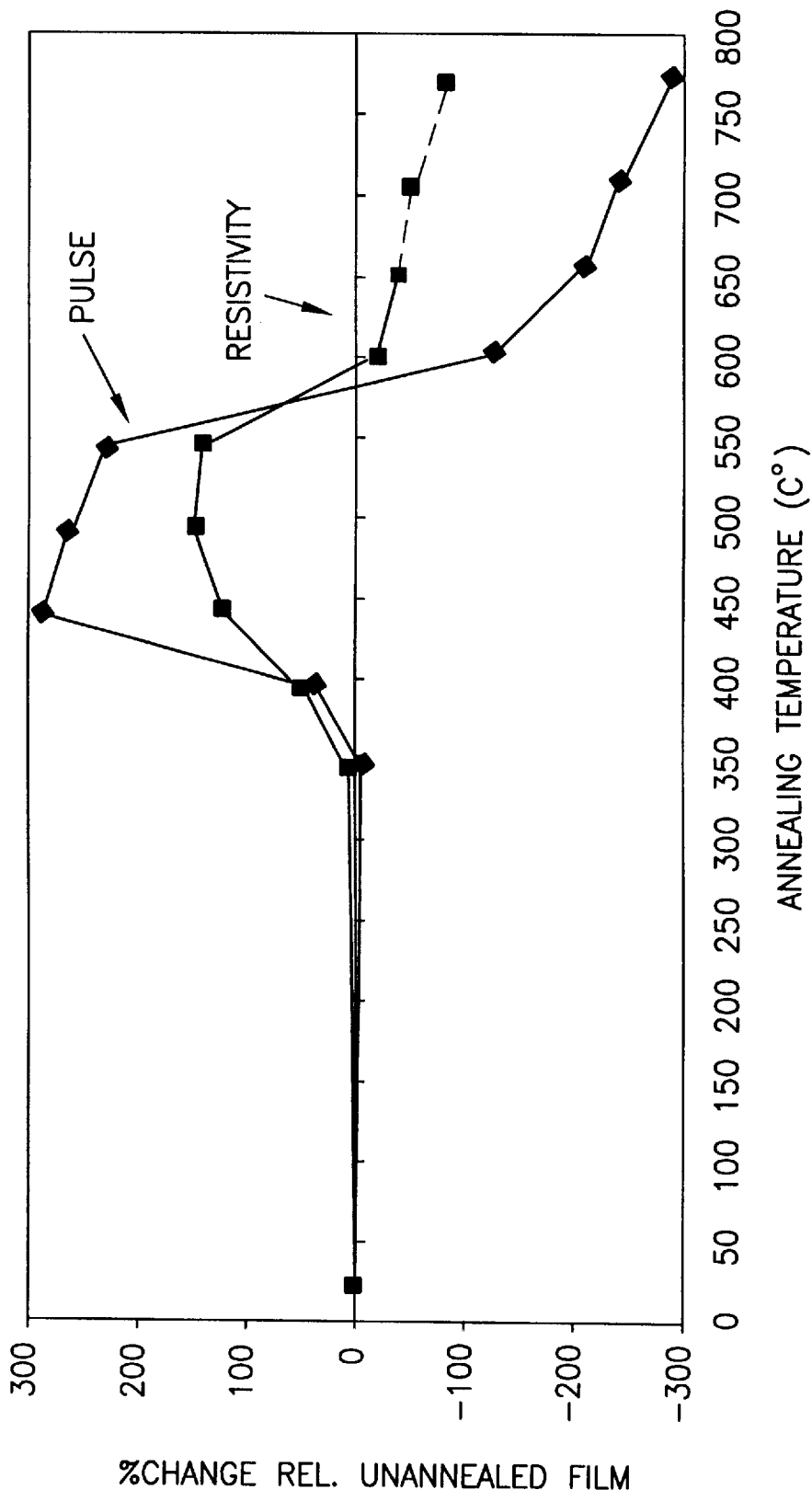
FIG. 6 is a graph illustrating a comparison of a picosecond reflectivity, from an arbitrary point on the curves shown in FIG. 4, versus annealing temperature, and which shows a correlation of this curve with a curve representing sheet resistivity.

Reference can now be had to FIGS. 4–6. A sample series consisted of 10 samples which had been subjected to a range of RTP (Rapid Thermal Processing) annealing temperatures. The annealing cycles differed slightly for different annealing temperatures.

A reaction between Ti and Si during the anneal cycle produces a layer whose electronic band structure changes as the reaction proceeds. The accompanying change in the transient reflectivity of the samples was measured in response to a short laser pulse, as described above. As was described above, there are two components of the measured signals. One component is a slowly varying "background" signal which is due to a combination of relaxation phenomena which take place after the laser pulse is absorbed by the film. The second component varies more rapidly, and is associated with acoustical vibrations of the layer. In accordance with an aspect of this invention, both components may be interpreted and used to characterize a given sample.

FIG. 4 is a graph which shows transient reflectivity signals measured for all samples. The temperatures at which the samples were annealed is indicated on the graph. The data show acoustical oscillations for times less than about 30 picoseconds which are superimposed on the slowly varying background signal. To simplify the discussion, the acoustical and background signals are separated, and the acoustical signals are plotted separately in FIG. 5. The curves in FIG. 5 have been intentionally offset from one another for the sake of clarity; and the ordering of the curves in FIG. 5 bears no relation to the ordering of the curves in FIG. 4 (to which no offsets have been applied).

Based on FIG. 4, from a qualitative perspective, it is clear that the 350° C. sample is substantially like the unannealed sample, from which it can be concluded that Ti and Si react very little at temperatures up to 350° C. There is some evidence in the acoustical signals that some change has occurred as a result of the 350° C. treatment, however, since the amplitudes of the "echoes" (for example, the "spiky" feature in the curve for the unannealed sample around 10 psec) is smaller for the 350° C. sample. This may be an indication that the interface has become roughened or blurred as a result of the annealing, and so makes a poorer acoustical reflector than the as-deposited Ti-Si interface. However, a large change can be seen to occur between 350° C. and 450° C. Based on the change in the background signal from negative to positive, and on the further weakening of the acoustical vibrations, it is clear that this change has begun to take place even at 400° C. By 450° C. the background signal has become strongly positive, and the acoustical signals have become quite strong. It is believed that this is an indication that a new layer has formed which is separated from the underlying Si substrate by a well-defined interface. Raman scattering data suggests that this is not a (C49) TiSi2 layer; nevertheless, the acoustics data suggests that, whatever the molecular structure, this layer is reasonably homogeneous. Between 450° C. and 550° C. the properties of the mixed layer slowly change. The acoustics signal becomes weaker and less regular than those observed at lower annealing temperatures, indicating the formation of internal structure within the layer. Between 550° C. and 600° C. there is a sudden change in both the background and the acoustics data. From the Raman data it was concluded that this change is associated with the sudden formation of the C49 phase. A slow increase in the thickness of this C49 layer is observed with further annealing up to 700° C., with a smaller change between 650° C. and 700° C. than between 600° C. and 650° C., which may suggest saturation. The increase in thickness is apparent from the shift to longer times of the acoustic peaks (which may be thought of as the vibrations of a slab, whose frequency becomes lower as its thickness is increased). Also observed was an increase in the amplitude of the acoustic signal, indicating that the interface between the $TiSi_2$ layer and the underlying Si becomes more distinct with annealing at higher temperatures. There is a final large change in the background signal for the sample annealed at 765° C., which the Raman data showed to be due to the formation of the C54 phase. The largest acoustical signal of the entire series was observed for this sample. It should also be noted that the rate of decay of the vibrations of the C54 film is smaller than that observed for the C49 samples, indicating that the interface between the C54 layer and Si may be smoother.

Figure 7A:
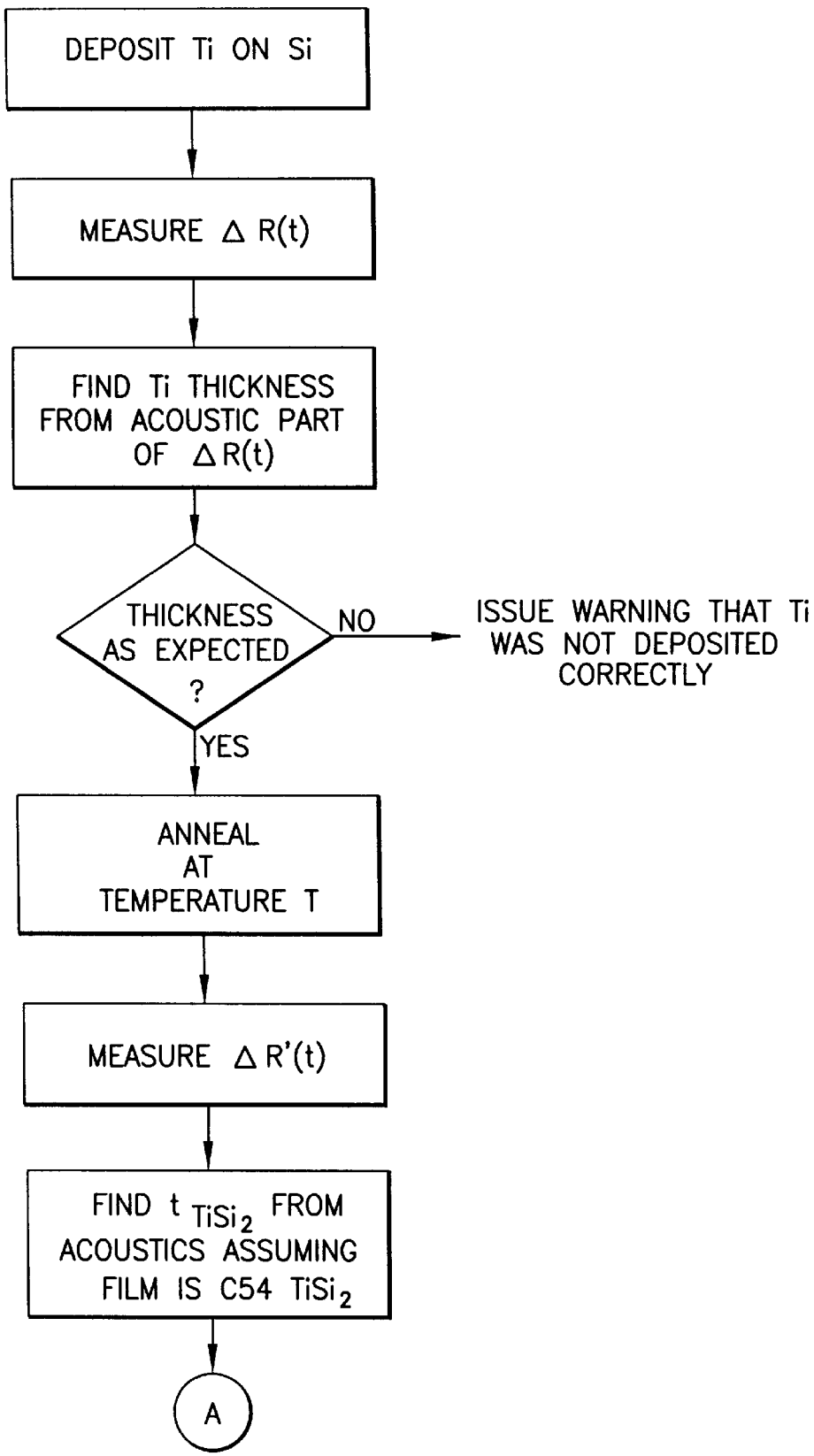
FIGS. 7A and 7B are a flow chart illustrating a method of this invention wherein an initial Ti thickness is known a priori.
Figure 7B:
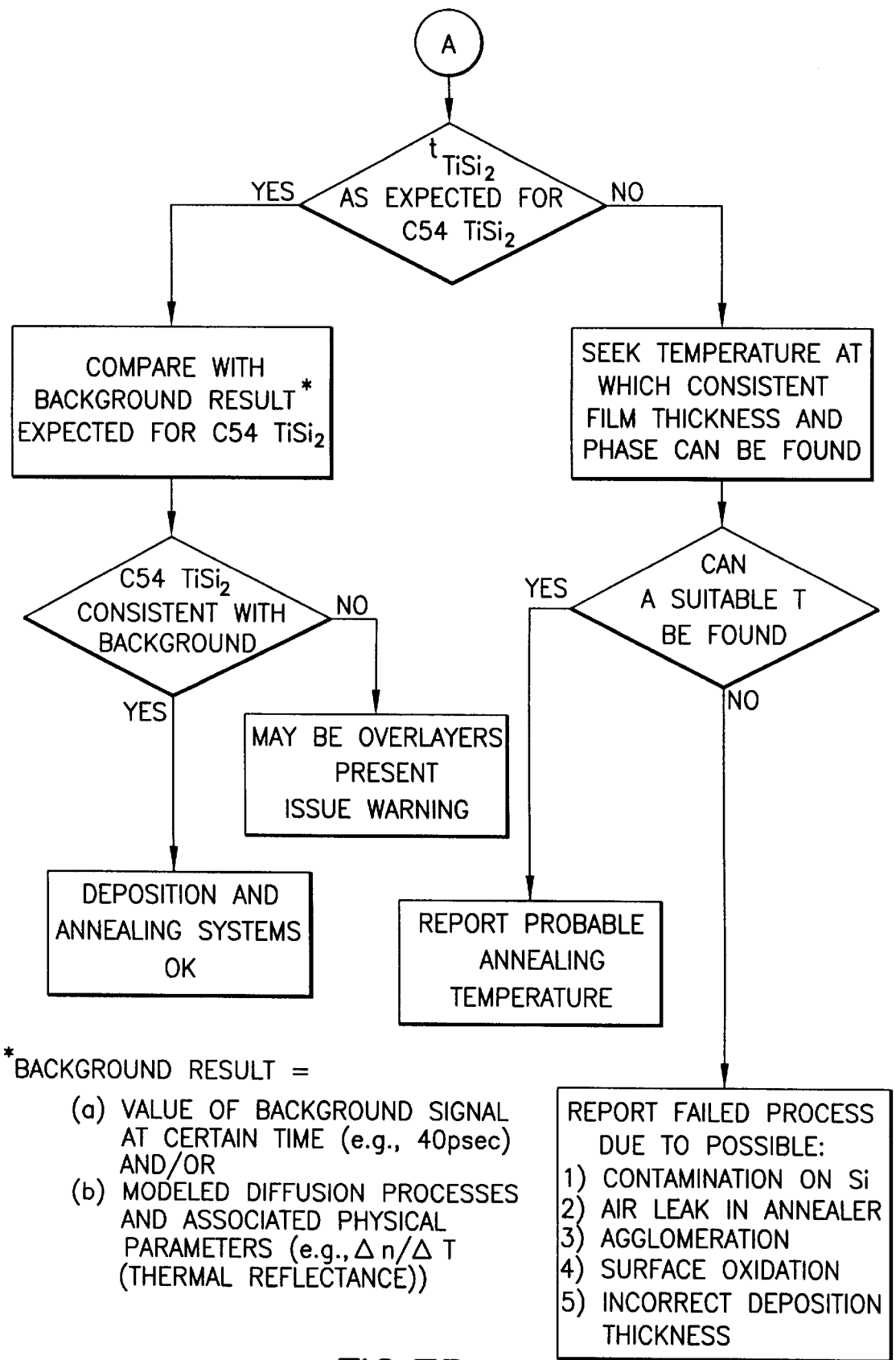

From the period of the acoustical oscillations of the as-deposited film and the known velocity of sound in titanium; the thickness of the Ti layer was determined to be 231 Å. For an ideal C54 TiSi2 layer, the corresponding theoretical thickness can be shown to be 580 Å. Assuming the 765° C. sample to be C54, a measured thickness of 581±3 Å was obtained, in very close agreement with the expected result. This is important because it shows how the acoustic information itself can be used to identify the silicide phase; i.e., the vibrational period of the silicide layer can be used as a measure of the completeness of the C54 formation if the initial Ti thickness is known. In this regard reference can be had to the flow chart of FIGS. 7A and 7B.

Qualitatively, curves similar to those in FIG. 4 are obtained for other thicknesses of Ti silicide, however, the details depend on the thickness to some degree.

There are at least two techniques that can be employed to provide an effective silicide monitor. A first technique, illustrated in FIGS. 7A and 7B, uses a family of reference curves corresponding to FIG. 4 for a starting target Ti thickness over a wide range of annealing temperatures. For a subsequent "unknown" sample having the same starting Ti thickness, the phase is determined by comparing its picosecond reflectivity with the reference curves.

A second technique employs a series of curves like those of FIG. 4, but corresponding to several thicknesses of Ti, and then determines the structural phase via Raman scattering (or any other suitable technique) for each curve. From this data the curves are constructed in accordance with the underlying physical parameters which govern the sign, amplitude, and rate of decay of the picosecond reflectivity for each phase.

Figure 8A:
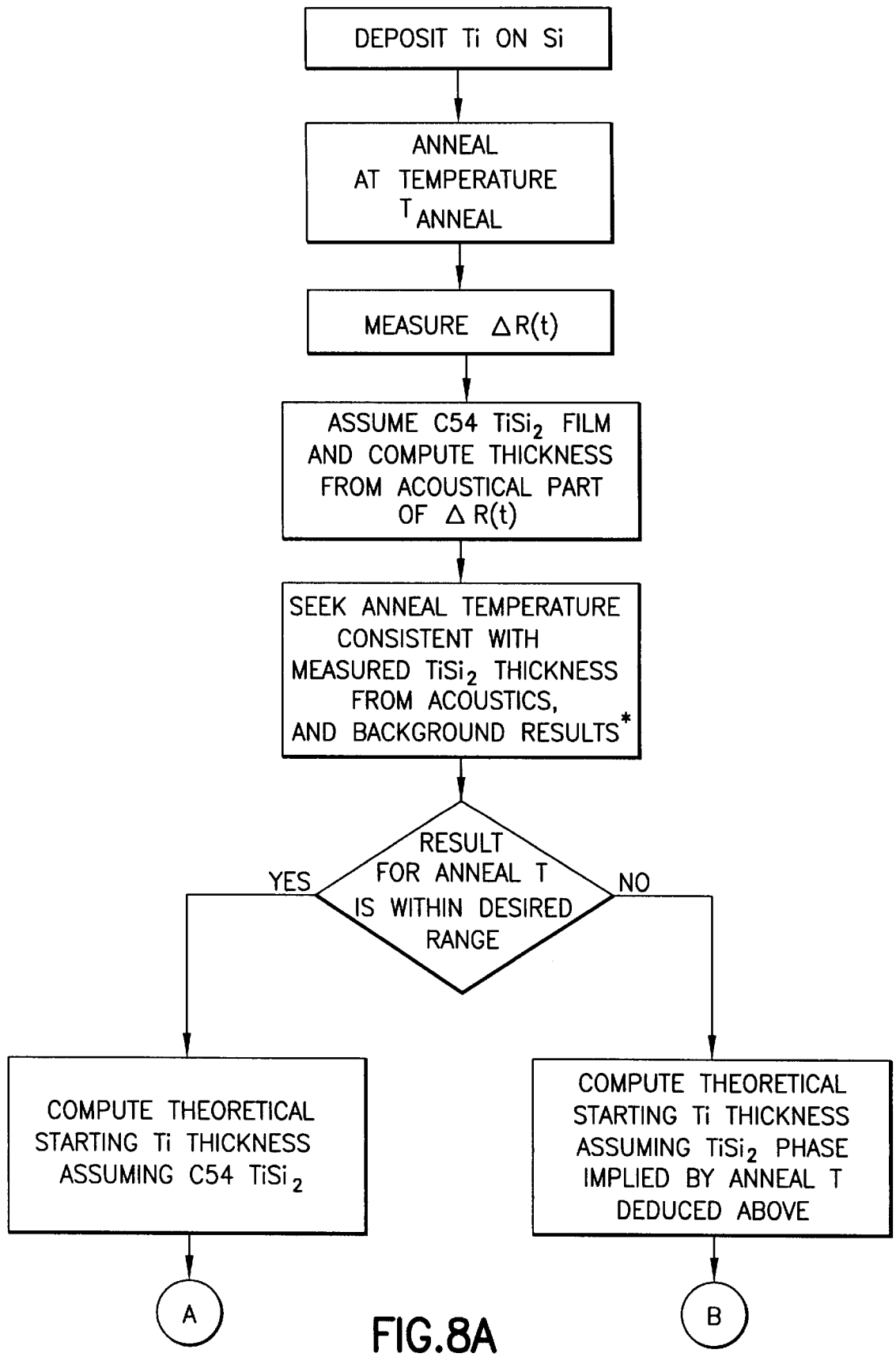
FIGS. 8A and 8B are a flow chart illustrating a method of this invention wherein an initial Ti thickness is not known a priori.
Figure 8B:
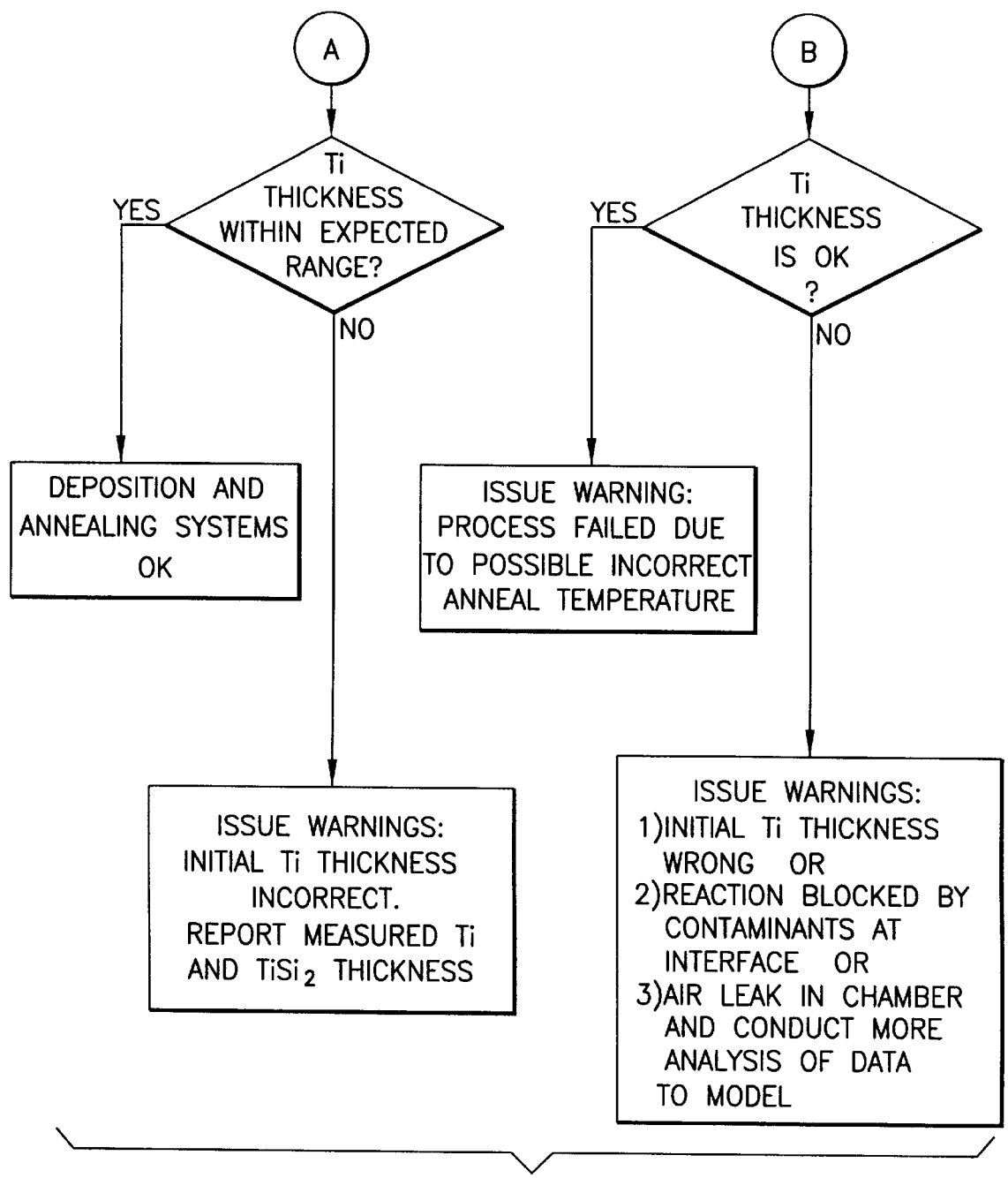

As can be seen in FIGS. 8A and 8B, for a subsequent "unknown" sample having any starting Ti thickness, the phase is determined by parametrizing its picosecond reflectivity in terms of the same parameters, and these parameters are then compared with their known values for each phase.

The second technique has the advantage of being potentially more transportable, although the first technique also provides satisfactory results.

As a simplified illustration of the operation of the first technique for the Ti thickness used in the present sample series (231 Å), the transient reflectivity change is plotted at an arbitrary point on the FIG. 4 curves versus the annealing temperature. The result is shown in FIG. 6. In constructing this Figure the transient reflectivity change at 45 picoseconds was used, expressed as a percentage change relative to the value obtained for the unannealed sample. The qualitative features of the curve correlate well with the graph of resistivity versus annealing temperature. As with the reflectivity data, the resistivities have been expressed as a percent change relative to the resistivity obtained for the unannealed sample.

The optical measurement system in accordance with this invention can be packaged as an in-fab optical metrology tool. It is completely nondestructive, and has a small spot size. For silicide monitoring it can be used to make measurements on product wafers within device or scribeline structures which are at least, by example, 5 microns in diameter. This value is a function of the particular focussing optics used. The use of fiber optic focussing optics, such as those having a reduced tip diameter, are especially attractive. Depending on such factors as pattern complexity and film thickness, measurement times range from, by example, 0.1 to 10 seconds per site. This technique can also be applied to small structures, such as regular arrays of lines and dots, using analogous analysis techniques.

An important aspect of the teaching of this invention is that it uses two independent components of the measured silicide response (i.e. the "background" signal and the "acoustical vibration" signal) to perform a self-consistent analysis. This readily distinguishes the technique of this invention from other silicide monitoring techniques which rely, for example, on resistivity or only reflectivity measurements. Self-consistent analysis allows the technique to not just detect a silicide misprocessing event, but to identify its cause. Whereas a sheet resistance measurement for a silicide can be misleading (for example, an out of control reading can arise because of variation of the deposited Ti layer, or because of incomplete silicide formation), the technique in accordance with this invention provides an unambiguous determination of the phase and thickness of an annealed film. It is ideally suited to high-throughput measurements on product wafers, and can produce high resolution film maps comparable to those obtained via four point probe measurements.

FIGS. 1A–1E illustrate various embodiments of sample measurement apparatus that are suitable for practicing this invention. These various embodiments are disclosed in copending U.S. patent application Ser. No. 08/689,287, filed Aug. 6, 1996, entitled "Improved Optical Stress Generator and Detector", by H. J. Maris and R. J. Stoner.

Figure 1A:
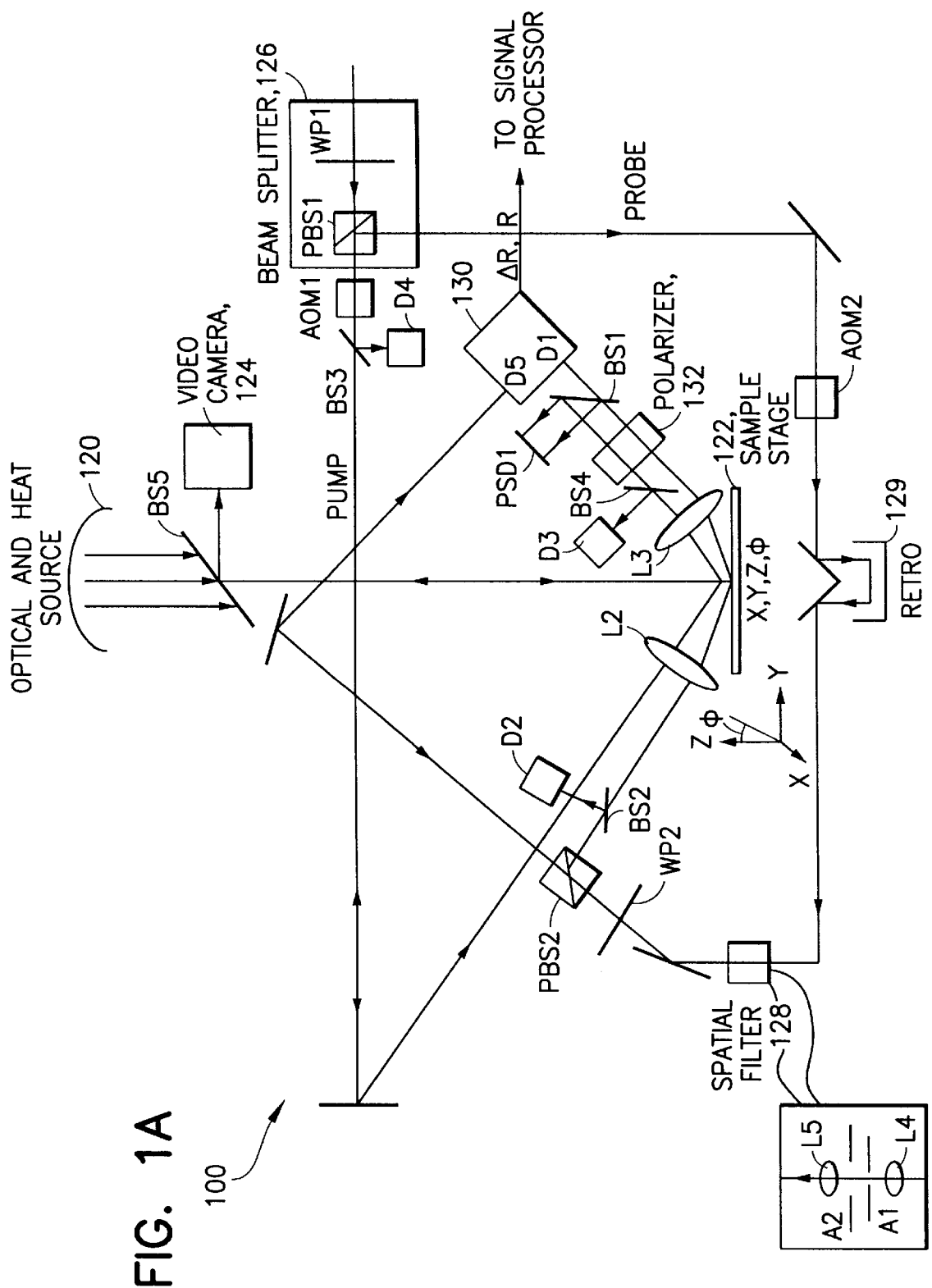
FIG. 1A is a block diagram of a first embodiment of a picosecond ultrasonic system that is suitable for use in practicing this invention, specifically, a parallel, oblique beam embodiment.

Reference is now made to FIG. 1A for illustrating an embodiment of apparatus 100 suitable for practicing this invention. The embodiment is referred to as a parallel, oblique embodiment.

This embodiment includes an optical/heat source 120, which functions as a variable high density illuminator, and which provides illumination for a video camera 124 and a sample heat source for temperature-dependent measurements under computer control. An alternative heating method employs a resistive heater embedded in a sample stage 122. The advantage of the optical heater is that it makes possible rapid sequential measurements at different temperatures. The video camera 124 provides a displayed image for an operator, and facilitates the set-up of the measurement system. Appropriate pattern recognition software can also be used for this purpose, thereby minimizing or eliminating operator involvement.

The sample stage 122 is preferably a multiple-degree of freedom stage that is adjustable in height (z-axis), position (x and y-axes), and tilt (θ), and allows motor controlled positioning of a portion of the sample relative to the pump and probe beams. The z-axis is used to translate the sample vertically into the focus region of the pump and probe, the x and y-axes translate the sample parallel to the focal plane, and the tilt axes adjust the orientation of the stage 122 to establish a desired angle of incidence for the probe beam. This is achieved via detector PSD1 and a local processor, as described below.

In an alternative embodiment, the optical head may be moved relative to a stationary, tiltable stage 122' (not shown). This is particularly important for scanning large objects (such as 300 mm diameter wafers, or mechanical structures, etc.) In this embodiment the pump beam, probe beam, and video signal can be delivered to or from the translatable head via optical fibers or fiber bundles.

BS5 is a broad band beam splitter that directs video and a small amount of laser light to the video camera 124. The camera 124 and local processor can be used to automatically position the pump and probe beams on a measurement site.

The pump-probe beam splitter 126 splits an incident laser beam pulse (preferably of picosecond or shorter duration) into pump and probe beams, and includes a rotatable half-wave plate (WP1) that rotates the polarization of the unsplit beam. WP1 is used in combination with polarizing beam splitter PBS1 to effect a continuously variable split between pump and probe power. This split may be controlled by the computer by means of a motor to achieve an optimal signal to noise ratio for a particular sample. The appropriate split depend on factors such as the reflectivity and roughness of the sample. Adjustment is effected by having a motorized mount rotate WP1 under computer control.

A first acousto-optic modulator (AOM1) chops the pump beam at a frequency of about 1 MHz. A second acousto-optic modulator (AOM2) chops the probe beam at a frequency that differs by a small amount from that of the pump modulator AOM1. The use of AOM2 is optional in the system illustrated in FIG. 1A. As will be discussed below, the AOMs may be synchronized to a common clock source, and may further be synchronized to the pulse repetition rate (PRR) of the laser that generates the pump and probe beams.

A spatial filter 128 is used to preserve at its output a substantially invariant probe beam profile, diameter, and propagation direction for an input probe beam which may vary due to the action of the mechanical delay line shown as a retroreflector 129. The spatial filter 128 includes a pair of apertures A1 and A2, and a pair of lenses L4 and L5. An alternative embodiment of the spatial filter incorporates an optical fiber, as described above.

WP2 is a second adjustable half wave plate which functions in a similar manner, with PBS2, to the WP1/PBS1 of the beamsplitter 126. With WP2 the intent is to vary the ratio of the part of the probe beam impinging on the sample to that of the portion of the beam used as a reference (input to D5 of the detector 130. WP2 may be motor controlled in order to achieve a ratio of approximately unity. The electrical signals produced by the beams are subtracted, leaving only the modulated part of the probe to be amplified and processed. PSD2 is used in conjunction with WP2 to achieve any desired ratio of the intensities of the probe beam and reference beam. The processor may adjust this ratio by making a rotation of WP2 prior to a measurement in order to achieve a nulling of the unmodulated part of the probe and reference beam. This allows the difference signal (the modulated part of the probe) alone to be amplified and passed to the electronics.

The beamsplitter BS2 is used to sample the intensity of the incident probe beam in combination with detector D2. The linear polarizer 132 is employed to block scattered pump light polarization, and to pass the probe beam. Lenses L2 and L3 are pump and probe beam focusing and collimating objectives respectively. The beamsplitter BS1 is used to direct a small part of pump and probe beams onto a first Position Sensitive Detector (PSD1) that is used for autofocusing, in conjunction with the processor and movements of the sample stage 122. The PSD1 is employed in combination with the processor and the computer-controlled stage 122 (tilt and z-axis) to automatically focus the pump and probe beams onto the sample to achieve a desired focusing condition.

The detector D1 may be used in common for transient optical, ellipsometry and reflectometry embodiments of this invention. However, the resultant signal processing is different for each application. For transient optical measurements, the DC component of the signal is suppressed, such as by subtracting reference beam input D5, or part of it as needed, to cancel the unmodulated part of D1, or by electrically filtering the output of D1 so as to suppress frequencies other than that of the modulation. The small modulated part of the signal is then amplified and stored. For ellipsometry, there is no small modulated part, rather the entire signal is sampled many times during each rotation of the rotation compensator (see FIG. 1B), and the resulting waveform is analyzed to yield the ellipsometric parameters. For reflectometry, the change in the intensity of the entire unmodulated probe beam due to the sample is determined by using the D1 and D2 output signals (D2 measures a signal proportional to the intensity of the incident probe). Similarly, additional reflectometry data can be obtained from the pump beam using detectors D3 and D4. The analysis of the reflectometry data from either or both beams may be used to characterize the sample. The use of two beams is useful for improving resolution, and for resolving any ambiguities in the solution of the relevant equations.

A third beamsplitter BS3 is used to direct a small fraction of the pump beam onto detector D4, which measures a signal proportional to the incident pump intensity. A fourth beamsplitter BS4 is positioned so as to direct a small fraction of the pump beam onto detector D3, which measures a signal proportional to the reflected pump intensity.

Figure 1B:
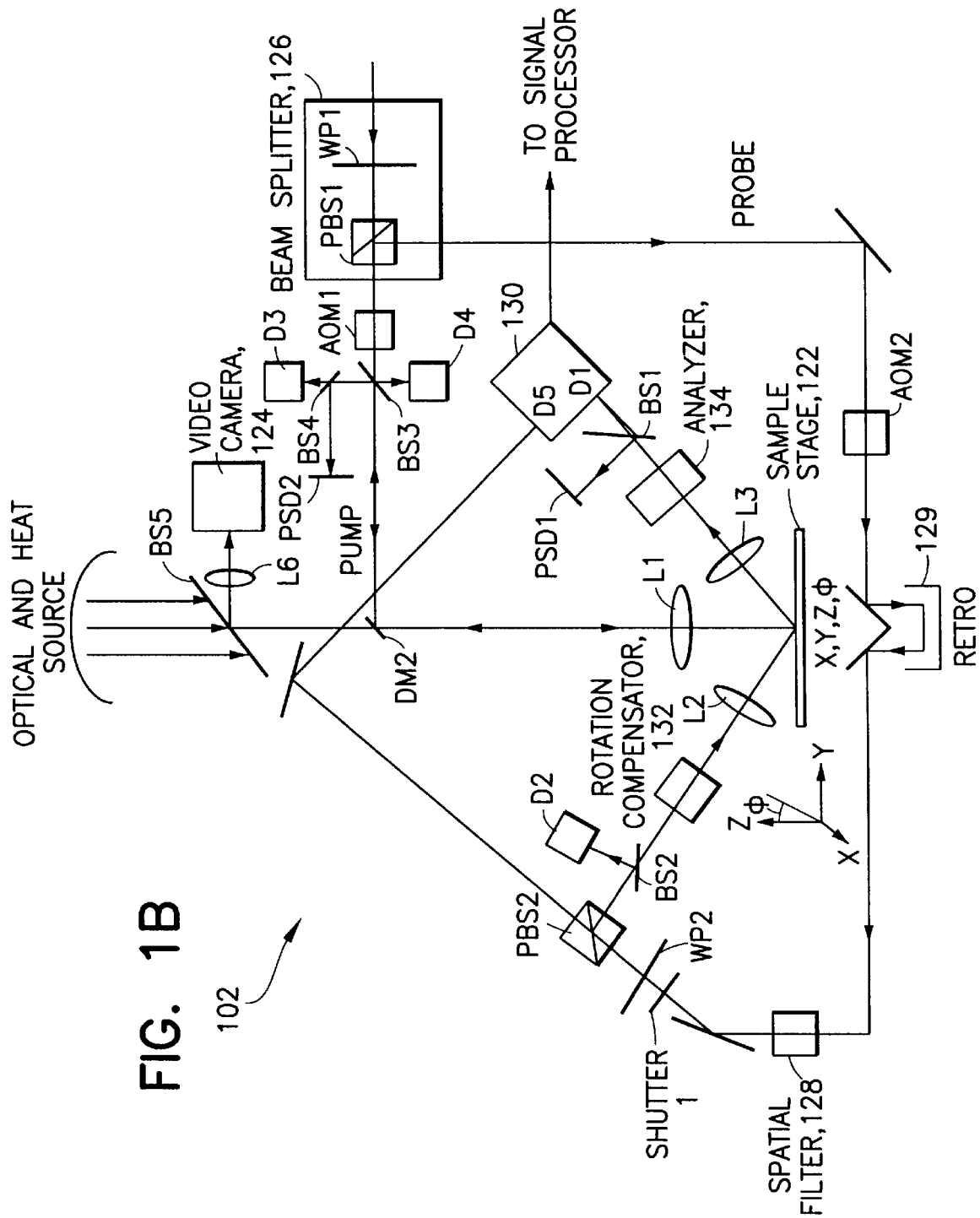
FIG. 1B is a block diagram of a second embodiment of a picosecond ultrasonic system that is suitable for use in practicing this invention, specifically, a normal pump, oblique probe embodiment.

FIG. 1B illustrates a normal pump beam, oblique probe beam embodiment of apparatus 102. Components labelled as in FIG. 1A function in a similar manner, unless indicated differently below. In FIG. 1B there is provided the above-mentioned rotation compensator 132, embodied as a linear quarter wave plate on a motorized rotational mount, and which forms a portion of an ellipsometer mode of the system. The plate is rotated in the probe beam at a rate of, by example, a few tens of Hz to continuously vary the optical phase of the probe beam incident on the sample. The reflected light passes through an analyzer 134 and the intensity is measured and transferred to the processor many times during each rotation. The signals are analyzed according to known types of ellipsometry methods to determine the characteristics of the sample (transparent or semitransparent films). This allows the (pulsed) probe beam to be used to carry out ellipsometry measurements.

The ellipsometry measurements are carried out using a pulsed laser, which is disadvantageous under normal conditions, since the bandwidth of the pulsed laser is much greater than that of a CW laser of a type normally employed for ellipsometry measurements.

If transient optical measurements are being made, the rotation compensator 132 is oriented such that the probe beam is linearly polarized orthogonal to the pump beam. The analyzer 134 may be embodied as a fixed polarizer, and also forms a portion of the ellipsometer mode of the system. When the system is used for transient optical measurements the polarizer 134 is oriented to block the pump beam.

The analyzer 134 may be embodied as a fixed polarizer, and also forms a portion of the ellipsometer mode of the system. When the system is used for acoustics measurements the polarizer 134 is oriented to block the pump polarization. When used in the ellipsometer mode, the polarizer 134 is oriented so as to block light polarized at 45 degrees relative to the plane of the incident and reflected probe beam.

The embodiment of FIG. 1B further includes a dichroic mirror (DM2), which is highly reflective for light in a narrow band near the pump wavelength, and is substantially transparent for other wavelengths.

It should be noted in FIG. 1B that BS4 is moved to sample the pump beam in conjunction with BS3, and to reflect a portion of the pump to D3 and to a second PSD (PSD2). PSD2 (pump PSD) is employed in combination with the processor, computer controlled stage 122 (tilt and z-axis), and PSD1 (Probe PSD) to automatically focus the pump and probe beams onto the sample to achieve a desired focusing condition. Also, a lens L1 is employed as a pump, video, and optical heating focussing objective, while an optional lens L6 is used to focus the sampled light from BS5 onto the video camera 124.

Figure 1C:
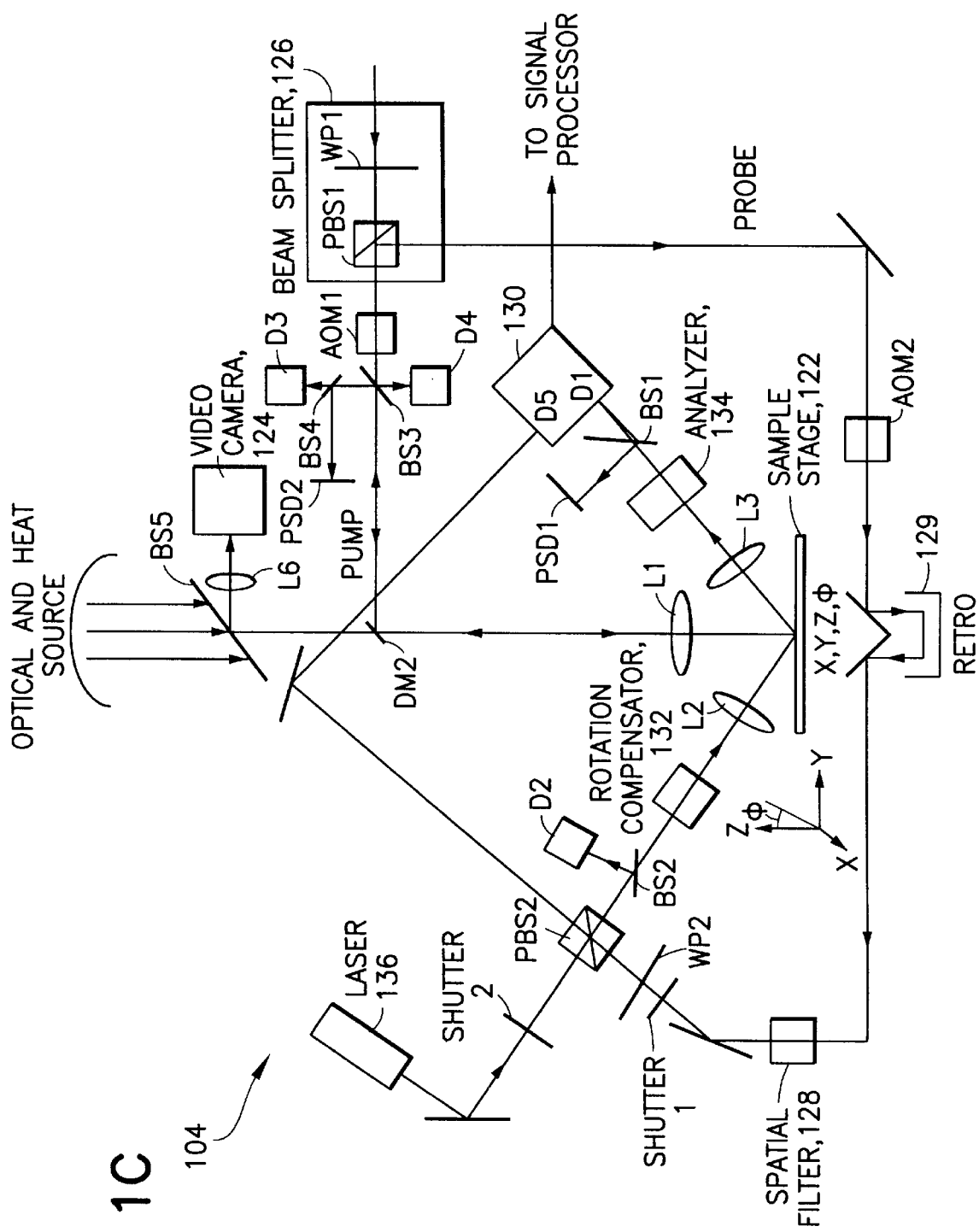
FIG. 1C is a block diagram of a third, presently preferred embodiment of a picosecond ultrasonic system that is suitable for use in practicing this invention, specifically, a single wavelength, normal pump, oblique probe, combined ellipsometer embodiment.

Reference is now made to FIG. 1C for illustrating an embodiment of apparatus 104, specifically a single wavelength, normal pump, oblique probe, combined ellipsometer embodiment. As before, only those elements not described previously will be described below.

Shutter 1 and shutter 2 are computer controlled shutters, and allow the system to use a He-Ne laser 136 in the ellipsometer mode, instead of the pulsed probe beam. For transient optical measurements shutter 1 is open and shutter 2 is closed. For ellipsometer measurements shutter 1 is closed and shutter 2 is opened. The HeNe laser 136 is a low power CW laser, and has been found to yield superior ellipsometer performance for some films.

Figure 1D:
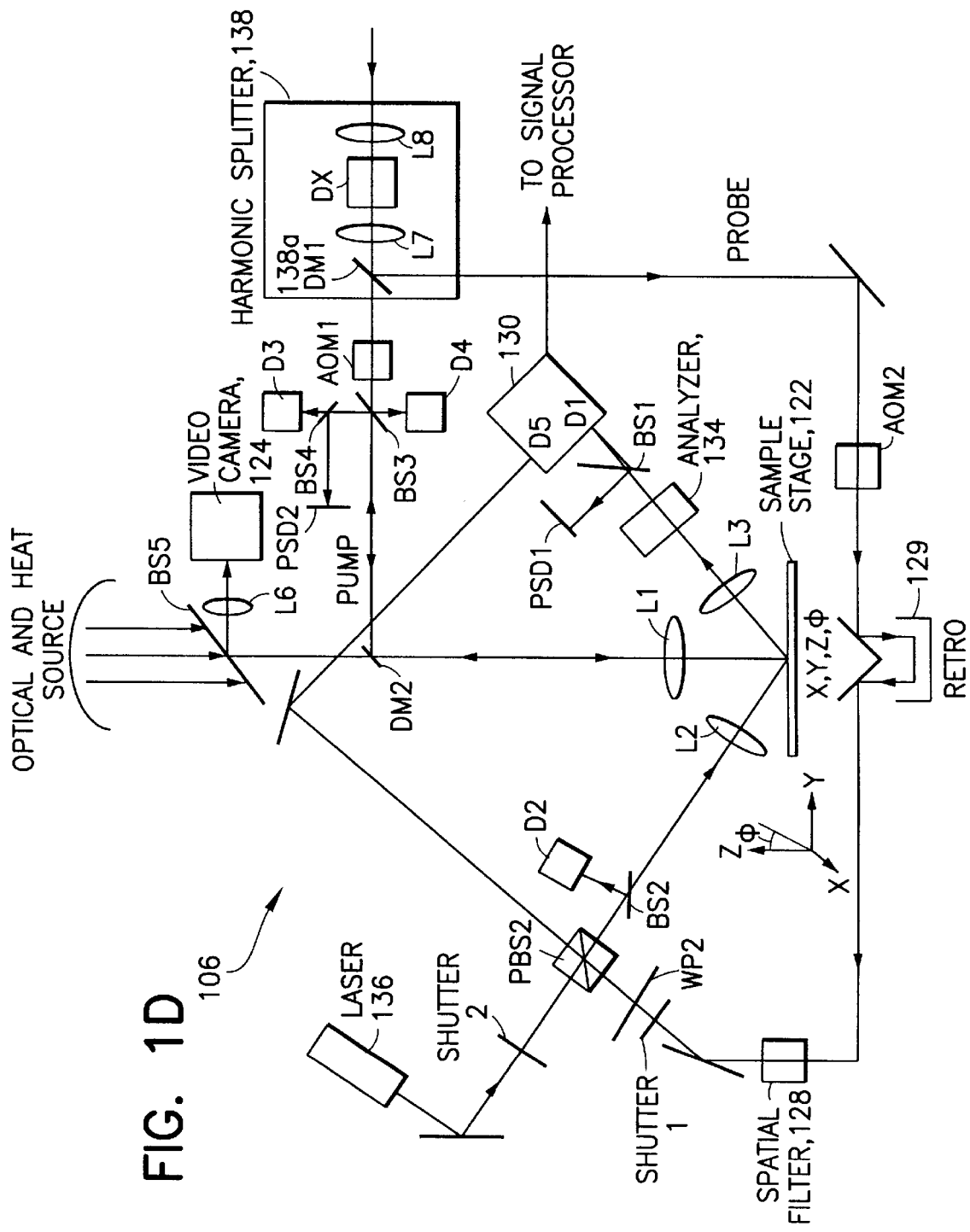
FIG. 1D is a block diagram of a fourth embodiment of a picosecond ultrasonic system that is suitable for use in practicing this invention, specifically, a dual wavelength, normal pump, oblique probe, combined ellipsometer embodiment.

FIG. 1D is a dual wavelength embodiment 1D of the system illustrated in FIG. 1C. In this embodiment the beamsplitter 126 is replaced by a harmonic splitter, an optical harmonic generator that generates one or more optical harmonics of the incident unsplit incident laser beam. This is accomplished by means of lenses L7, L8 and a nonlinear optical material (DX) that is suitable for generating the second harmonic from the incident laser beam. The pump beam is shown transmitted by the dichroic mirror (DM 138a) to the AOM1, while the probe beam is reflected to the retroreflector. The reverse situation is also possible. The shorter wavelength may be transmitted, and the longer wavelength may be reflected, or vice versa. In the simplest case the pump beam is the second harmonic of the probe beam (i.e., the pump beam has one half the wavelength of the probe beam).

It should be noted that in this embodiment the AOM2 is eliminated since rejection of the pump beam is effected by means of color filter F1, which is simpler and more cost effective than heterodyning. F1 is a filter having high transmission for the probe beam and the He-Ne wavelengths, but very low transmission for the pump wavelength.

Figure 1E:
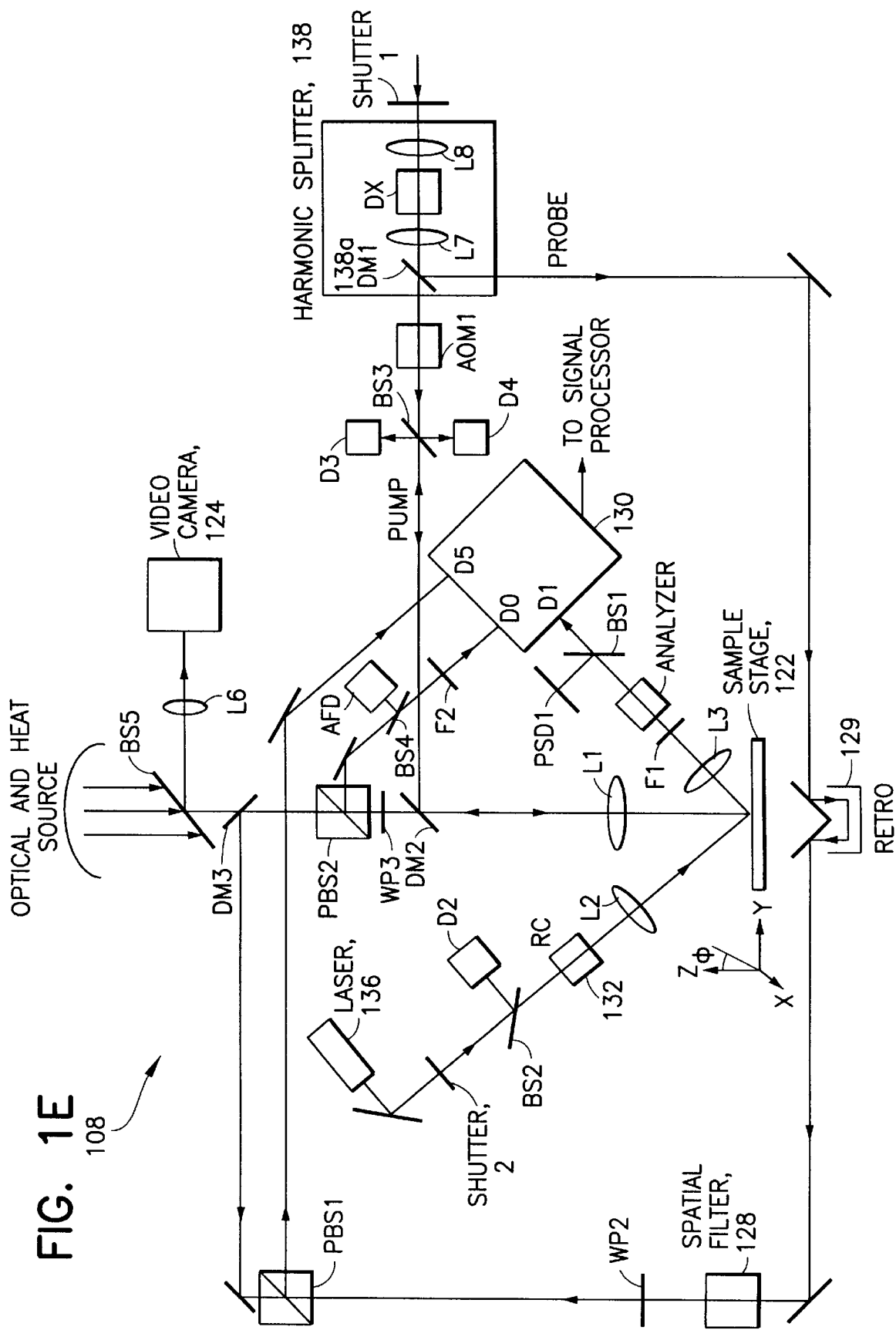
FIG. 1E is a block diagram of a fifth embodiment of a picosecond ultrasonic system that is suitable for use in practicing this invention, specifically, a dual wavelength, normal incidence pump and probe, combined ellipsometer embodiment.
Figure 3:
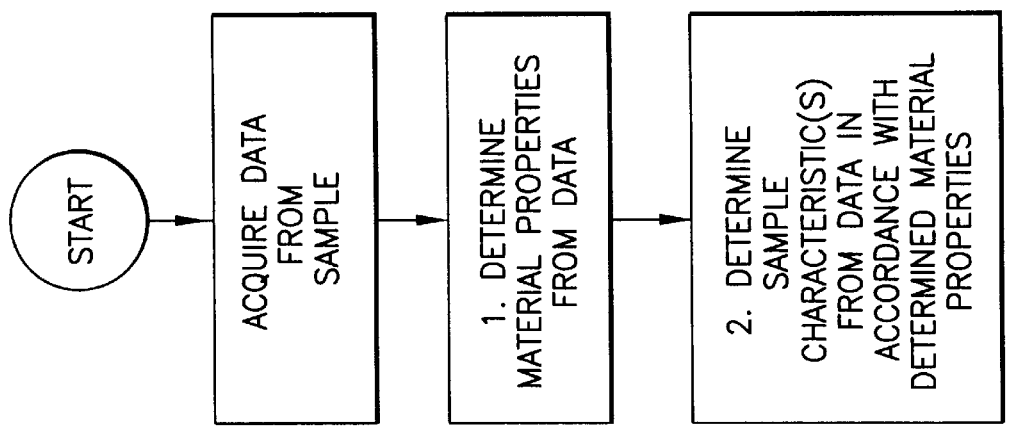
FIG. 3 is a flow chart that illustrates a method in accordance with this invention.

Finally, FIG. 1E illustrates a normal incidence, dual wavelength, combined ellipsometer embodiment 108. In FIG. 1E the probe beam impinges on PBS2 and is polarized along the direction which is passed by the PBS2. After the probe beam passes through WP3, a quarter wave plate, and reflects from the sample, it returns to PBS2 polarized along the direction which is highly reflected, and is then directed to a detector D0 in detector block 130. D0 measures the reflected probe beam intensity.

In greater detail, WP3 causes the incoming plane polarized probe beam to become circularly polarized. The handedness of the polarization is reversed on reflection from the sample, and on emerging from WP3 after reflection, the probe beam is linearly polarized orthogonal to its original polarization. BS4 reflects a small fraction of the reflected probe onto an Autofocus Detector AFD.

DM3, a dichroic mirror, combines the probe beam onto a common axis with the illuminator and the pump beam. DM3 is highly reflective for the probe wavelength, and is substantially transparent at most other wavelengths. D1, a reflected He-Ne laser 136 detector, is used only for ellipsometric measurements.

It should be noted that, when contrasting FIG. 1E to FIGS. 1C and 1D, that the shutter 1 is relocated so as to intercept the incident laser beam prior to the harmonic splitter 138.

Based on the foregoing descriptions, a selected one of these presently preferred embodiments of measurement apparatus provide for the characterization of samples in which a short optical pulse (the pump beam) is directed to an area of the surface of the sample, and then a second light pulse (the probe beam) is directed to the same or an adjacent area at a later time. The retroreflector 129 shown in all of the illustrated embodiments of FIGS. 1A–1E can be employed to provide a desired temporal separation of the pump and probe beams.

The apparatus 100, 102, 104, 106 and 108 is capable of measuring some or all of the following quantities: (1) the small modulated change $\Delta R$ in the intensity of the reflected probe beam, (2) the change $\Delta T$ in the intensity of the transmitted probe beam, (3) the change $\Delta P$ in the polarization of the reflected probe beam, (4) the change $\Delta \phi$ in the optical phase of the reflected probe beam, and/or (5) the change in the angle of reflection $\Delta \beta$ of the probe beam. These quantities (1)–(5) may all be considered as transient responses of the sample which are induced by the pump pulse. These measurements can be made together with one or several of the following: (a) measurements of any or all of the quantities (1)–(5) just listed as a function of the incident angle of the pump or probe light, (b) measurements of any of the quantities (1)–(5) as a function of more than one wavelength for the pump and/or probe light, (c) measurements of the optical reflectivity through measurements of the incident and reflected average intensity of the pump and/or probe beams; (d) measurements of the average phase change of the pump and/or probe beams upon reflection; and/or (e) measurements of the average polarization and optical phase of the incident and reflected pump and/or probe beams. The quantities (c), (d) and (e) may be considered to be average or static responses of the sample to the pump beam.

It is within the scope of this invention to employ computer simulations to calculate the change in the optical reflectivity $\Delta R_{sim}(t)$ of the sample when it is illuminated with a pump pulse of unit energy per unit area of the sample. The simulation may also give a value for the static reflection coefficient of the pump and probe beams. The system measures the transient change $\Delta P_{probe\text{-}refl}$ in the power of the reflected probe pulse as determined, for example, by photodiode D1 in FIG. 1C. It also measures the static reflection coefficients of the pump and probe beams from a ratio of the power in the incident and reflected beams. The incident probe power is measured by photodiode D2 in FIG. 1C, the reflected probe power is measured by D1, the incident pump power is measured by D4, and the reflected pump power is measured by D3.

To relate such simulation results for the transient change in the optical reflectivity to the actual system measurement it is necessary to know: (a) the power of the pump and probe beams; (b) the intensity profiles of these beams; and (c) their overlap on the sample surface.

Let us suppose first that the pump beam is incident over an area $A_{pump}$ and that within this area the pump intensity is uniform. Then for each applied pump pulse the pump energy absorbed per unit area is:

$$\frac{P_{pump\text{-}inc}}{A_{pump}} \frac{(1 - R_{pump})}{f} \quad (1)$$

where f is the repetition rate of the pump pulse train, and $R_{pump}$ is the reflection coefficient for the pump beam.

Thus, the change in optical reflectivity of the each probe light pulse will be:

$$\Delta R_{sim}(t) \frac{P_{pump\text{-}inc}}{A_{pump}} \frac{(1 - R_{pump})}{f} \quad (2)$$

and the change in power of the reflected probe beam will be $$\Delta P_{probe\text{-}refl} = P_{probe\text{-}inc} \Delta R_{sim}(t) \frac{P_{pump\text{-}inc}}{A_{pump}} \frac{(1 - R_{pump})}{f} \quad (3)$$

In a practical system the illumination of the sample does not, in fact, produce a uniform intensity of the incident pump beam. Moreover, the intensity of the probe light will also vary with position on the sample surface. To account for these variations the equation for $\Delta P_{probe\text{-}refl}$ is modified to read:

$$\Delta P_{probe\text{-}refl} = P_{probe\text{-}inc} \Delta R_{sim}(t) \frac{P_{pump\text{-}inc}}{A_{effective}} \frac{(1 - R_{pump})}{f} \quad (4)$$

where the effective area $A_{effective}$ is defined by the relation $$A_{effective} = \frac{\int I_{pump\text{-}inc}(\vec{r}) dA \int I_{probe\text{-}inc}(\vec{r}) dA}{\int I_{pump\text{-}inc}(\vec{r}) I_{probe\text{-}inc}(\vec{r}) (dA)} \quad (5)$$

where $I_{probe\text{-}inc}(\vec{r})$ and $I_{pump\text{-}inc}(\vec{r})$ are respectively the intensities of the probe and pump beams on the surface of the sample. One amy consider $A_{effective}$ to be an effective area of overlap of the pump and probe beams.

Analogous expressions can be derived for the change in optical transmission $\Delta T(t)$, the change in optical phase $\Delta\phi(t)$, the change in polarization $\Delta P(t)$, and the change $\Delta\beta(t)$ in the angle of reflection of the probe light.

The following quantities are measured by the system: $\Delta P_{probe\text{-}refl}$, $P_{probe\text{-}inc}$, $P_{pump\text{-}inc}$, $R_{pump}$, $R_{probe}$. A computer simulation gives predicted values for $\Delta R_{sim}(t)$, $R_{pump}$, and $R_{probe}$. Thus, the following comparisons can be made between the simulation and the system measurements in order to determine the characteristics of the sample.

(1) A comparison of the simulated and measured reflection coefficient $R_{pump}$.

(2) A comparison of the simulated and measured reflection coefficient $R_{probe}$.

(3) A comparison of the simulated and measured transient change $\Delta P_{probe\text{-}refl}$ in the power of the reflected probe light.

To make a comparison of the simulated and measured change, it can be seen from the preceding equation (4) that it is necessary to know the value of $A_{effective}$. This can be accomplished by one or more of the following methods.

(a) A first method directly measures the intensity variations of the pump and probe beams over the surface of the sample, i.e, $I_{probe\text{-}inc}(\vec{r})$ and $I_{pump}(\vec{r})$ as a function of position, and uses the results of these measurements to calculate $A_{effective}$. This is possible to accomplish but requires very careful measurements which may be difficult to accomplish in an industrial environment.

(b) A second method measures the transient response $\Delta P_{probe\text{-}refl}$ for a sample on a system S for which the area $A_{effective}$ is known. This method then measures the response $\Delta P_{probe\text{-}refl}$ of the same sample on the system S' for which $A_{effective}$ is to be determined. The ratio of the responses on the two systems gives the inverse of the ratio of the effective areas for the two systems. This can be an effective method because the system S can be chosen to be a specially constructed system in which the areas illuminated by the pump and probe beams are larger than would be desirable for an instrument with rapid measurement capability. Since the areas are large for this system it is simpler to measure the intensity variations of the pump and probe beams over the surface of the sample, i.e, $I_{probe\text{-}inc}(\vec{r})$ and $I^{pump\text{-}inc}(\vec{r})$ as a function of position. This method is effective even if the quantities which enter into the calculation of the simulated reflectivity change $\Delta R_{sim}(t)$ are not known.

(c) A third method measures the transient response $\Delta P_{probe\text{-}refl}$ for a sample in which all of the quantities are known which enter into the calculation of the simulated reflectivity change $\Delta R_{sim}(t)$ of the sample when it is illuminated with a pump pulse of unit energy per unit area of the sample. Then by comparison of the measured transient response $\Delta P_{probe\text{-}refl}$ with the response predicted from the Eq. 6, the effective area $A_{effective}$ is determined.

It is important that the effective area $A_{effective}$ be stable throughout the course of a sequence of measurements. To ensure this, the apparatus shown in FIGS. 1A–1E incorporate means for automatically focusing the pump and probe beams onto the surface of the sample so as to achieve a reproducible intensity variation of the two beams during every measurement. The automatic focusing system provides a mechanism for maintaining the system in a previously determined state in which the size and relative positions of the beams on the sample surface are appropriate for effective transient response measurements.

It should be noted that for any application in which the amplitude of an optical transient response is used to draw quantitative conclusions about a sample (for example, when the magnitude of the background signal is influenced by the phase of a material), a calibration scheme such as described above is an important feature of the measurement system, wherein calibration includes determining a size and an area of overlap of the pump and probe beams on a surface of the sample.

The preceding description of the method for the comparison of the computer simulation results and the system measurements supposes that the several detectors in the measurement system are calibrated. It is contemplated that such a system will use detectors operating in the linear range so that the output voltage V of each detector is proportional to the incident optical power P. For each detector there is thus a constant G such that V=GP. The preceding description assumes that the constant G is known for each and every detector. In the case that this information is not available, the individual calibration factors associated with each of the individual detectors measuring $P_{probe-inc}$, $P_{pump-inc}$, and $\Delta P_{probe-refl}$ may be combined with $A_{effective}$ and f into a single overall system calibration constant C. Therefore in terms of a calibration factor C, Eq. 4 could be expressed as $$\Delta V_{probe-refl} = C\ V_{probe-inc}\ \Delta R_{sim}(t)\ V_{pump-inc}\ (1-R_{pump}) \qquad (6),$$

where $\Delta V_{probe-refl}$ is the output voltage from the detector used to measure the change in the power of the reflected probe light (D1), $V_{pumpinc}$ is the output voltage from the detector used to measure the incident pump light (D4), and $V_{probe-inc}$ is the output voltage of the detector used to measure the incident probe light (D2). Thus, it is sufficient to determine the constant C. This can be accomplished by either of the following two methods.

(a) A first method measures the transient response $\Delta V_{probe-refl}$ for a sample in which all of the quantities are known which enter into the calculation of the simulated reflectivity change $\Delta R_{sim}(t)$ of the sample, when it is illuminated with a pump pulse of unit energy per unit area of the sample. Next, the method measures $V_{probe-inc}$ and $V_{pump-inc}$, then determines $R_{pump}$ either by measurement or from the computer simulation. The method then finds the value of the constant C such that Eq. 6 is satisfied.

(b) A second method measures the transient response $\Delta V_{probe-refl}$ for a reference sample for which the transient optical response $\Delta R(t)$, when it is illuminated with a pump pulse of unit energy per unit area of the sample, has been measured using a system which has been previously calibrated, for example, by one or more of the methods described above. The method then measure $V_{probe-inc}$ and $V_{pump-inc}$, determines $R_{pump}$ by measurement, and then finds the value of the constant C such that the following equation is satisfied:

$$\Delta V_{probe-refl} = C\ V_{probe-inc}\ \Delta R(t)\ V_{pump-inc}\ (1=R_{pump}) \qquad (7)$$

For both of these methods it is important to establish the autofocus conditions prior to making measurements of $\Delta V_{probe-refl}$, since C depends on the value of $A_{effective}$.

In view of the foregoing, it can be appreciated that this invention employs an analysis of the background and acoustical data from a sample in order to get a best result for two sample properties, namely the thickness and the composition of the material comprising a thin film, wherein the term "composition" is herein intended to include characteristics such as phase, morphology, crystalline orientation, grain size, etc.

The analysis may assume a value for one of the properties, and then determine the other by simulation and/or by comparison to data obtained from known reference samples. The analysis may also be self-consistent by assuming a value for one property, then determining the other by simulation and/or by comparison to data obtained from known reference samples, then improving the value for the assumed property, and then continuing to iterate until to obtain a best result for both properties. For example, this iteration can be begun by first assuming a thickness of the film, and then determining the film's composition, or by first assuming a composition for the film and then determining the thickness. Both are equally valid approaches.

By example, in a first method the following steps are executed.

(A) Calibrate the measurement system, such as that shown in FIG. 1C, autofocus, and measure the sample.

(B) Assume a value for the thickness (d) of the film.

(C) Compare the background signal corresponding to a film of the same general type (e.g., $TiSi_2$) having the assumed thickness to determine a most probable composition for the film. This implies the use of a specific set of material properties, such as sound velocity, density, optical constants such as n and $\kappa$, thermal expansion coefficient, specific heat, thermal conductivity, the derivatives of n and $\kappa$ with respect to strain, etc. By example, the material properties for 46-54 TiN differ from the material properties for 47-53 TiN.

(D) Associate the physical properties of the film from step C with the sample film.

(E) Deduce an improved value for d from an analysis of the acoustical part of the data.

(F) Optionally repeat steps B–E until convergence (a correct answer) is obtained.

In a second method the following steps are executed.

(A) Calibrate the measurement system, autofocus, and measure the sample.

(B) Assume a composition of the film (e.g., 50—50 TiN).

(C) Deduce a value for the thickness from an analysis of the acoustical part of the data.

(D) Compare the background signal corresponding to a film of the same general type (e.g., TiN) having the assumed thickness to determine an improved composition for the film. This again implies the use of a specific set of material properties, such as sound velocity, density, optical constants and derivatives with respect to strain, etc.

(E) Associate the physical properties of the film from step C with the sample film.

(F) Optionally repeat steps B-E until convergence is obtained.

In a third method, a simplified variant of the first, the following steps are executed.

(A) Calibrate the measurement system, such as that shown in FIG. 1C, autofocus, and measure the sample.

(B) Assume a value for the thickness (d) of the film.

(C) Compare the background signal corresponding to a film of the same general type having the assumed thickness to determine a most probable composition for the film.

(D) Associate the physical properties of the film from step C with the sample film.

In a fourth method, a simplified variant of the second, the following steps are executed.

(A) Calibrate the measurement system, autofocus, and measure the sample.

(B) Assume a composition of the film.

(C) Deduce a value for the thickness from an analysis of the acoustical part of the data.

(D) Associate the physical properties of the film from step C with the sample film.

Any of the forgoing steps of comparing can optionally interpolate between reference data or parameters that are measured or deduced from a plurality of reference samples.

Furthermore, the methods can include a step of modifying an assumed composition of the sample or film by one or more of the stoichiometry, crystal structure, morphology, structural phase, alloy composition, impurity content, doping level, defect density, isotope content, grain orientation, etc.

The teaching of this invention can also be employed with compound semiconductors, such as Group III–V and Group II–VI compound semiconductors, having an unknown content of one or more constituent elements.

The teaching of this invention is especially beneficial for use with samples comprised of a semiconductor material and a metal or silicide. Related to the foregoing, the teaching of this invention is also useful with samples comprised of an alloy of at least two elements having an unknown ratio. Examples include Ti-W, Au-Cr, Al-Cu, Al-Cu-Si, Si-Ge, In-Ga-As, Ga-Al-As, and Hg-Cd-Te.

The methods of this invention are particularly useful with thermally annealed samples for determining annealing temperature, the thickness of an annealed layer, and the phase of an annealed layer.

This invention can be employed to advantage with a wide range of materials and material systems having a finite (useable) absorption of the pump wavelength that is sufficient to excite strain waves in the sample. As was described above in reference to the embodiment shown in FIG. 1D, the wavelengths of the pump and probe pulses may be different.

Thus, while the invention has been particularly shown and described with respect to preferred embodiments thereof, it will be understood by those skilled in the art that changes in form and details may be made therein without departing from the scope and spirit of the invention.

What is claimed is:

1. A method for characterizing a sample, comprising the steps of:
    acquiring data from the sample using at least one probe beam wavelength to measure, for a range of delay times, a change in at least one transient optical response of the sample induced by a pump beam;
    analyzing the data to determine at least one material property of the sample by comparing a background signal component of the data with data obtained for a similar delay time range from one or more samples prepared under conditions known to give rise to certain physical and chemical material properties; and
    analyzing a component of the measured change in the at least one transient optical response, using the at least one determined material property, to determine at least one sample property of interest, wherein the component results from ultrasonic waves generated by the pump beam.

2. A method as set forth in claim 1, wherein the one or more samples prepared under conditions known to give rise to certain physical and chemical material properties are reference samples, and wherein the first step of analyzing includes a step of interpolating between the data obtained for the reference samples to determine an intermediate set of material properties.

3. A method as set forth in claim 1, wherein the material properties include at least one of sound velocity, density, optical constants, thermal expansion coefficient, specific heat, thermal conductivity, and derivatives of optical constants with respect to strain.

4. A method as set forth in claim 1 wherein the at least one of the sample properties of interest includes stoichiometry, crystal structure, morphology, structural phase, alloy composition, impurity content, doping level, defect density, isotope content, and grain orientation of the sample.

5. A method as set forth in claim 1, and comprising an initial step of calibrating a measurement system that is used to acquire the data, the step of calibrating including a step of determining a size and an area of overlap of the pump and probe beams on a surface of the sample.

6. A method as set forth in claim 1, wherein the at least one transient optical response includes one of a measurement of a modulated change $\Delta R$ in an intensity of a reflected portion of a probe pulse, a change $\Delta T$ in an intensity of a transmitted portion of the probe pulse, a change $\Delta P$ in a polarization of the reflected probe pulse, a change $\Delta\phi$ in an optical phase of the reflected probe pulse, and a change in an angle of reflection $\Delta\beta$ of the probe pulse.

7. A method for characterizing a sample, comprising the steps of:
    acquiring data from the sample using at least one probe beam wavelength to measure, for a range of delay times, a change in at least one transient optical response of the sample induced by a pump beam;
    analyzing the data to determine a sample preparation technique by comparing a background signal component of the data with data obtained for a similar delay time range from one or more reference samples prepared by similar sample preparation techniques; and
    analyzing a component of the measured change in at least one transient optical response using data corresponding to the determined sample preparation technique to determine at least one sample property of interest, wherein the component results from ultrasonic waves generated by the pump beam.

8. A method as set forth in claim 7, wherein the sample is comprised of a wafer that includes semiconductor material and a metal.

9. A method as set forth in claim 7, wherein the sample is comprised of a wafer that includes semiconductor material and a silicide.

10. A method as set forth in claim 7, wherein the first step of analyzing includes a step of interpolating between data obtained for reference samples.

11. A method as set forth in claim 7, and comprising an initial step of calibrating a measurement system that is used to acquire the data, the step of calibrating including a step of establishing a size and an area of overlap of the pump and probe beams on a surface of the sample.

12. A method as set forth in claim 7, wherein the at least one transient optical response includes one of a measurement of a modulated change $\Delta R$ in an intensity of a reflected portion of a probe pulse, a change $\Delta T$ in an intensity of a transmitted portion of the probe pulse, a change $\Delta P$ in a polarization of the reflected probe pulse, a change $\Delta\phi$ in an optical phase of the reflected probe pulse, and a change in an angle of reflection $\Delta\beta$ of the probe pulse.

13. A non-destructive system for characterizing a sample to determine at least one sample property of interest, comprising:
    means for generating a sequence of pump pulses and a sequence of probe pulses and for directing said pulses to a surface of a sample;
    means for acquiring data from the sample, using at least one probe pulse wavelength, to measure, for a range of delay times between individual ones of the pump and probe pulses, a change in at least one transient optical response of the sample induced by the pump pulse; and
    means for analyzing the data to determine at least one material property of the sample by comparing a background signal component of the data with data corresponding to a similar range of delay times for one or more reference samples prepared under conditions known to give rise to certain physical and chemical material properties, said analyzing means further being operable for analyzing a component of the measured change in at least one transient optical response, caused by ultrasonic waves generated by the pump pulse, using the at least one determined material property, for determining the at least one sample property of interest.

14. A system as set forth in claim 13, wherein said analyzing means includes means for interpolating between data obtained from a plurality of reference samples.

15. A system as set forth in claim 13, wherein said material properties include at least one of sound velocity, density, optical constants, thermal expansion coefficient, specific heat, thermal conductivity, and derivatives of optical constants with respect to strain.

16. A system as set forth in claim 13, in which the at least one of the sample properties of interest includes stoichiometry, crystal structure, morphology, structural phase, alloy composition, impurity content, doping level, defect density, isotope content, and grain orientation of the sample.

17. A system as set forth in claim 13, and further comprising means for calibrating said system, said calibrating means including means for establishing a size and an area of overlap of the pump and probe pulses on the surface of the sample.

18. A system as set forth in claim 13, wherein the at least one transient optical response includes one of a measurement of a modulated change $\Delta R$ in an intensity of a reflected portion of a probe pulse, a change $\Delta T$ in an intensity of a transmitted portion of the probe pulse, a change $\Delta P$ in a polarization of the reflected probe pulse, a change $\Delta \phi$ in an optical phase of the reflected probe pulse, and a change in an angle of reflection $\Delta \beta$ of the probe pulse.

19. A system as set forth in claim 13, wherein the data corresponding to a similar range of delay times is generated from at least one of: (a) at least one reference sample; and (b) a modeled diffusion process and associated physical parameters.

20. A system as set forth in claim 13, wherein the sample is comprised of a wafer that includes semiconductor material and a silicide.

21. A system as set forth in claim 13, wherein the sample is comprised of a wafer that includes semiconductor material and a metal.

22. A system as set forth in claim 13, wherein the sample is comprised of a wafer that includes a substrate and at least one thermally annealed layer disposed over a surface of the substrate.

23. A system as set forth in claim 22, wherein the analyzing means reports a probable annealing temperature of the at least one thermally annealed layer.

24. A system as set forth in claim 22, wherein the analyzing means reports a presence or absence of an expected phase associated with the at least one thermally annealed layer.

25. A system as set forth in claim 22, wherein the analyzing means reports a thickness of the at least one thermally annealed layer.

26. A method of characterizing a sample, comprising the steps of:
(A) acquiring data from the sample using at least one probe beam wavelength to measure, for a range of delay times, a change in at least one transient optical response of the sample induced by a pump beam;
(B) assuming a value for a thickness of the sample;
(C) comparing a background signal, resulting from a non-acoustical component of the acquired data, to data that corresponds to a reference sample having the assumed thickness, to determine a most probable composition for the sample; and
(D) associating material properties of the sample, determined as a result of the execution of step C, with the reference sample.

27. A method as set forth in claim 26, and further comprising the step of:
(E) deducing an improved value for the thickness from an analysis of an acoustical component of the acquired data.

28. A method as set forth in claim 27, and further comprising the step of:
(F) repeating steps C–E until convergence between the sample thickness and the material properties is achieved.

29. A method as set forth in claim 26, wherein the step of determining the most probable composition for the sample includes a step of interpolating between data obtained for reference samples to determine a set of material properties of the sample.

30. A method as set forth in claim 29, wherein the material properties of the sample include at least one of sound velocity, density, optical constants, thermal expansion coefficient, specific heat, thermal conductivity, and derivatives of optical constants with respect to strain.

31. A method as set forth in claim 26, in which at least one of the material properties of the sample includes stoichiometry, crystal structure, morphology, structural phase, alloy composition, impurity content, doping level, defect density, isotope content, and grain orientation.

32. A method as set forth in claim 26, wherein the at least one transient optical response includes one of a measurement of a modulated change $\Delta R$ in an intensity of a reflected portion of a probe pulse, a change $\Delta T$ in an intensity of a transmitted portion of the probe pulse, a change $\Delta P$ in a polarization of the reflected probe pulse, a change $\Delta \phi$ in an optical phase of the reflected probe pulse, and a change in an angle of reflection $\Delta \beta$ of the probe pulse.

33. A method as set forth in claim 26, wherein the step of comparing uses data corresponding to a range of delay times generated from at least one of: (a) at least one reference sample; and (b) a modeled diffusion process and associated physical parameters.

34. A method as set forth in claim 26, wherein the sample is comprised of a wafer that includes semiconductor material and a silicide.

35. A method as set forth in claim 26, wherein the sample is comprised of a wafer that includes semiconductor material and a metal.

36. A method as set forth in claim 26, wherein the sample is comprised of a wafer that includes a substrate and at least one thermally annealed layer disposed over a surface of the substrate.

37. A method as set forth in claim 36, and further comprising a step of reporting a probable annealing temperature of the at least one thermally annealed layer.

38. A method as set forth in claim 36, and further comprising a step of reporting a presence or absence of an expected phase associated with the at least one thermally annealed layer.

39. A method as set forth in claim 36, and further comprising a step of reporting a thickness of the at least one thermally annealed layer.

40. A method as set forth in claim 26, and comprising an initial step of calibrating a measurement system that is used to acquire the data, the step of calibrating including a step of determining a size and an area of overlap of the pump and probe beams on a surface of the sample.

41. A method of characterizing a sample, comprising the steps of:
(A) acquiring data from the sample using at least one probe beam wavelength to measure, for a range of delay times, a change in at least one transient optical response of the sample induced by a pump beam;
(B) assuming a composition of the sample;
(C) deducing a value for a thickness of the sample from an analysis of an acoustical part of the data, the step of deducing including a step of considering the sample's material properties based on a reference sample having the assumed composition; and
(D) comparing a background signal corresponding to the reference sample having the deduced thickness, wherein results of the comparison are used to determine an improved composition for the sample.

42. A method as set forth in claim 41, and further comprising a step of:
(E) associating material properties of the sample from step D with the reference sample.

43. A method as set forth in claim 42, and further comprising a step of:
(F) repeating steps C–E until convergence between the sample's composition and the material properties is achieved.

44. A method as set forth in claim 41, wherein the step of determining an improved composition of the sample includes a step of interpolating between data obtained for reference samples to determine a set of material properties of the sample.

45. A method as set forth in claim 41, wherein the material properties include at least one of sound velocity, density, optical constants, thermal expansion coefficient, specific heat, thermal conductivity, and derivatives of optical constants with respect to strain.

46. A method as set forth in claim 41, in which the composition of the sample includes at least one of the stoichiometry, crystal structure, morphology, structural phase, alloy composition, impurity content, doping level, defect density, isotope content, and grain orientation.

47. A method as set forth in claim 41, wherein the at least one transient optical response includes one of a measurement of a modulated change $\Delta R$ in an intensity of a reflected portion of a probe pulse, a change $\Delta T$ in an intensity of a transmitted portion of the probe pulse, a change $\Delta P$ in a polarization of the reflected probe pulse, a change $\Delta \phi$ in an optical phase of the reflected probe pulse, and a change in an angle of reflection $\Delta \beta$ of the probe pulse.

48. A method as set forth in claim 41, wherein the step of comparing uses data corresponding to a range of delay times generated from at least one of: (a) at least one reference sample; and (b) a modeled diffusion process and associated physical parameters.

49. A method as set forth in claim 41, wherein the sample is comprised of a wafer that includes semiconductor material and a silicide.

50. A method as set forth in claim 41, wherein the sample is comprised of a wafer that includes semiconductor material and a metal.

51. A method as set forth in claim 41, wherein the sample is comprised of a wafer that includes a substrate and at least one thermally annealed layer disposed over a surface of the substrate.

52. A method as set forth in claim 51, and further comprising a step of reporting a probable annealing temperature of the at least one thermally annealed layer.

53. A method as set forth in claim 51, and further comprising a step of reporting a presence or absence of an expected phase associated with the at least one thermally annealed layer.

54. A method as set forth in claim 51, and further comprising a step of reporting a thickness of the at least one thermally annealed layer.

55. A method as set forth in claim 41, and comprising an initial step of calibrating a measurement system that is used to acquire the data, the step of calibrating including a step of determining a size and an area of overlap of the pump and probe beams on a surface of the sample.

\* \* \* \* \*